United States Patent
Hume et al.

(10) Patent No.: US 9,240,002 B2
(45) Date of Patent: Jan. 19, 2016

(54) SYSTEMS AND METHODS FOR A GRAPHICAL INTERFACE INCLUDING A GRAPHICAL REPRESENTATION OF MEDICAL DATA

(75) Inventors: James A. Hume, Deerfield, IL (US); Robert M. Hume, legal representative, Charlotte, NC (US); Robert Mayer, Arlington Heights, IL (US); Devy Amy Lee, Round Beach, IL (US); Gabriele Ott, Bainbridge Island, WA (US); Candida Arvelo, Flower Mound, TX (US); Timothy L. Ruchti, Gurnee, IL (US); Tamas Ban, Round Lake Beach, IL (US); Mohammad M. Khair, Streamwood, IL (US); Nancy H. Hedlund, Libertyville, IL (US)

(73) Assignee: Hospira, Inc., Lake Forest, IL (US)

(*) Notice: Subject to any disclaimer, the term of this patent is extended or adjusted under 35 U.S.C. 154(b) by 439 days.

(21) Appl. No.: 13/588,026

(22) Filed: Aug. 17, 2012

(65) Prior Publication Data

US 2013/0047113 A1 Feb. 21, 2013

Related U.S. Application Data

(60) Provisional application No. 61/525,418, filed on Aug. 19, 2011.

(51) Int. Cl.
*G06F 3/048* (2013.01)
*G06Q 10/10* (2012.01)
*G06Q 50/22* (2012.01)
*G06F 19/00* (2011.01)

(52) U.S. Cl.
CPC ............ *G06Q 10/10* (2013.01); *G06F 19/3468* (2013.01); *G06F 19/3487* (2013.01); *G06Q 50/22* (2013.01); *A61M 2205/502* (2013.01); *A61M 2205/52* (2013.01); *G06F 19/345* (2013.01); *G06F 19/3443* (2013.01)

(58) Field of Classification Search
CPC .................. A61M 2205/502; A61M 2205/52; G06F 19/3468; G06F 19/3487; G06F 19/3418
USPC .......................................... 715/771
See application file for complete search history.

(56) References Cited

U.S. PATENT DOCUMENTS

| | | | | |
|---|---|---|---|---|
| 5,486,286 A | * | 1/1996 | Peterson | ............... A61M 1/16 210/321.65 |
| 7,213,009 B2 | | 5/2007 | Pestotnik | |

(Continued)

OTHER PUBLICATIONS

Smith, Joe, Infusion Pump Informatics, CatalyzeCare: Transforming Healthcare, at least as early as May 12, 2011, p. 1-2, online—catalyzecare.org.

(Continued)

*Primary Examiner* — Dino Kujundzic
(74) *Attorney, Agent, or Firm* — Michael R. Crabb

(57) ABSTRACT

This disclosure describes systems and methods for a graphical interface including a graphical representation of medical data. The graphical interface platform may receive medical data and provide medical safety reporting capabilities including reporting of history data and real-time visual monitoring data. The graphical interface platform may be configured to identify potential problems and corrections to medical devices in operation while a reporting cycle is underway through visual representation of performance metrics.

18 Claims, 16 Drawing Sheets

(56) References Cited

U.S. PATENT DOCUMENTS

| | | |
|---|---|---|
| 7,230,529 B2 | 6/2007 | Ketcherside |
| 7,447,643 B1 | 11/2008 | Olson |
| 7,523,401 B1* | 4/2009 | Aldridge .................. 715/760 |
| 7,705,727 B2 | 4/2010 | Pestotnik |
| 2002/0038392 A1* | 3/2002 | De La Huerga ................ 710/8 |
| 2003/0052787 A1 | 3/2003 | Zerhusen et al. |
| 2004/0172222 A1* | 9/2004 | Simpson ............ G06F 19/3418 702/189 |
| 2004/0172283 A1 | 9/2004 | Vanderveen |
| 2004/0172302 A1* | 9/2004 | Martucci ............. A61B 5/0002 705/2 |
| 2004/0181314 A1 | 9/2004 | Zaleski |
| 2005/0055242 A1 | 3/2005 | Bello |
| 2005/0137653 A1 | 6/2005 | Friedman et al. |
| 2005/0144043 A1* | 6/2005 | Holland ............... G06F 19/326 705/3 |
| 2006/0064020 A1* | 3/2006 | Burnes et al. .................. 600/481 |
| 2006/0229557 A1* | 10/2006 | Fathallah ........... G06F 19/3406 604/131 |
| 2006/0229918 A1 | 10/2006 | Fotsch |
| 2007/0100665 A1 | 5/2007 | Brown |
| 2008/0033361 A1* | 2/2008 | Evans .................. A61M 5/172 604/151 |
| 2008/0091466 A1 | 4/2008 | Butler |
| 2008/0300572 A1* | 12/2008 | Rankers et al. ................ 604/504 |
| 2009/0005703 A1* | 1/2009 | Fasciano ...................... 600/561 |
| 2009/0054743 A1* | 2/2009 | Stewart ........................ 600/301 |
| 2009/0149743 A1* | 6/2009 | Barron et al. ................. 600/431 |
| 2009/0177769 A1* | 7/2009 | Roberts ........................ 709/224 |
| 2010/0121415 A1* | 5/2010 | Skelton et al. .................. 607/62 |
| 2010/0131434 A1* | 5/2010 | Magent et al. ................... 706/11 |
| 2010/0271479 A1 | 10/2010 | Heydlauf |
| 2011/0001605 A1* | 1/2011 | Kiani et al. ..................... 340/5.6 |
| 2011/0004620 A1* | 1/2011 | Butler .................. G06F 19/327 707/769 |
| 2011/0072379 A1 | 3/2011 | Gannon |
| 2011/0078608 A1* | 3/2011 | Gannon et al. ................ 715/771 |

OTHER PUBLICATIONS

CareAware Infusion Management, Cerner Store, at least as early as May 12, 2011, p. 1-3, online—https://store.cernter.com/items/7.

\* cited by examiner

Dashboards

Welcome! John Smith
Security Level: Unrestricted
Role: Nursing, Historical
ADVANCED Mode    Logout

| Infusion (Text) | Infusion (Graph-Simple) | Infusion (Graph-Advanced) | ExecScoreCard | Pareto Tables | Rule Set Optimizer | Drug Library Optimizer |

Print

High-level Infuser Information

| CCA | Pump Name | DL in use | Alert Status | Alarm Status | High-risk Med | Power Status |
|-----|-----------|-----------|--------------|--------------|---------------|--------------|
| ICU | ICU_PCA-1 | Yes | PCA Avail. | None | YES | 100% |
| ICU | ICU_PlumA+_1 | No | NONE | Distal occlusion | YES | 100% (A/C) |
| ICU | ICU_Symbiq_1 | Yes | NONE | None | YES | 25% |
| ICU | ICU_PCA_1 | Yes | PCA locked out | Peridant fault | YES | 100% |
| ICU | ICU_PlumA+_1 | Yes | NONE | VTBI Complete | YES | 100% (A/C) |
| ICU | ICU_Symbiq_1 | Yes | NONE | Bag was empty | YES | 50% |
| ICU | ICU_PCA_1 | Yes | NONE | None | YES | 100% |
| ICU | ICU_PCA_1 | No | NONE | None | YES | 100% (A/C) |

Infuser Location and Infusion Therapy Information

| Asset No. | Pump Name | Medication | Concentration | Dose | Rate | VTBI | Volume Remaining | Rule Sets |
|-----------|-----------|------------|---------------|------|------|------|------------------|-----------|
| W12300 | PCA | Morphine | 1 mg/mL | 5 mcg/kg/min | 8.4 mL/hr | 250 mL | 153 mL | Dose Rate |
| W12301 | PlumA+ | Dobutamine | 500 mg/250 mL | 1 mg/min | 33.3 mL/hr | 500 mL | 423 mL | Dose Rate |
| W12302 | PlumA+ | Amiodarone | 900 mg/500 mL | 2,000 Units/hr | 40 mL/hr | 500 mL | 230 mL | Dose Rate |
| W12303 | PlumA+ | Heparin | 25,000 Units/500 mL | 10 mEq/hr | 50 mL/hr | 50 mL | 27 mL | Dose Rate |
| W12304 | PlumA+ | KCL Rider 10 mEq | 10 mEq/50 mL | N/A | 400 mL/hr | 1,000 mL | 980 mL | Bolus Rate |
| W12305 | Symbiq | NaCl 0.9% | N/A | N/A | N/A | N/A | N/A | N/A |
| W12306 | PCA | N/A | N/A | N/A | N/A | N/A | N/A | N/A |
| W12307 | PlumA+ | Precedex | 200 mcg/50 mL | 0.5 mcg/kg/hr | 300 mL/hr | 50 mL | 24 mL | Dose Rate |

**** County General Hospital    1:34 PM    Current User: John Smith    Symbiq Drug Library Compliance: +9% ICU | +6% PEDS | -2% L&D | +14% PreOp    PlumA+ Drug Library

FIG. 3

Dashboards

Welcome! John Smith
Security Level: Unrestricted
Role: Nursing, Historical
ADVANCED Mode    Logout

| Infusion (Text) | Infusion (Graph-Simple) | Infusion (Graph-Advanced) | ExecScoreCard | Pareto Tables | Rule Set Optimizer | Drug Library Optimizer |

CCA-ALL ▽  Infuser-ALL ▽

Infuser - ALL Scorecard

1/17/20 — 02/17/20   [Print]

Summary

| DL Compliance | # of Total Programs | Total Alerts | Overrides | Edits | Upper Soft Limit Alerts | Lower Soft Limit Alert | Upper Hard Limit Alerts | Lower Hard Limit Alerts |
|---|---|---|---|---|---|---|---|---|
| 97.6% | 124,268 | 6,164 | 4,305 | 1,859 | 4,381 | 1,114 | 475 | 194 |

Total Alerts by Medication - Top 10 - Medications Infused

| Medication/Concentrations | Total Programs | Alerts | % Alerts to Programs | # Overrides | # Edits |
|---|---|---|---|---|---|
| IV Fluid | 33,852 | 2,177 | 6.4% | 1,786 | 391 |
| Heparin 25,000 Units/250 mL | 4,319 | 437 | 10.1% | 230 | 207 |
| Insulin 250 Units/250 mL | 3,295 | 69 | 2.1% | 42 | 27 |
| Propofol 1,000 mg/100 mL | 2,393 | 145 | 6.1% | 86 | 59 |
| IVF - No Additives | 1,398 | 13 | 0.9% | 0 | 13 |
| IVF Fluid (50kg or more) | 1,392 | 145 | 10.4% | 127 | 18 |
| Potassium Chloride 20 mEq/50 mL | 1,107 | 139 | 12.6% | 115 | 24 |
| Antibiotic - Any Volume | 1,025 | 17 | 1.7% | 1 | 16 |
| Phenylephrine 10 mg/250 mL | 827 | 106 | 12.8% | 65 | 41 |

+

1%PEDS | 0% L&D | -2%

FIG. 9

Dashboards

Welcome! John Smith
Security Level: Unrestricted
Role: Nursing, Historical
ADVANCED Mode    Logout

| Infusion (Text) | Infusion (Graph-Simple) | Infusion (Graph-Advanced) | ExecScoreCard | Pareto Tables | Rule Set Optimizer | Drug Library Optimizer |

Infuser - ALL Scorecard

CCA-ALL ▼    Infuser-ALL ▼                    1/17/20  -  02/17/20

Summary

| DL Compliance | # of Total Programs | Total Alerts | Overrides | Edits | Upper Limit A... | | Lower Hard Limit Alerts |
|---|---|---|---|---|---|---|---|
| 97.6% | 124,268 | 6,164 | 4,305 | 1,859 | 4,3... | | 194 |

Total Alerts by Medication - Top 10 - Medications In...

February, 20
| Sun | Mon | Tue | Wed | Thu | Fri | Sat |
|---|---|---|---|---|---|---|
| 30 | 31 | 1 | 2 | 3 | 4 | 5 |
| 6 | 7 | 8 | 9 | 10 | 11 | 12 |
| 13 | 14 | 15 | 16 | 17 | 18 | 19 |
| 20 | 21 | 22 | 23 | 24 | 25 | 26 |
| 27 | 28 | 1 | 2 | 3 | 4 | 5 |
| 6 | 7 | 8 | 9 | 10 | 11 | 12 |

Today: 2/17/20

| Medication/Concentrations | Total Programs | Alerts | % Alerts to Programs | # Overrides | # Edits |
|---|---|---|---|---|---|
| IV Fluid | 33,852 | 2,177 | 6.4% | 1,786 | 391 |
| Heparin 25,000 Units/250 mL | 4,319 | 437 | 10.1% | 230 | 207 |
| Insulin 250 Units/250 mL | 3,295 | 69 | 2.1% | 42 | 27 |
| Propofol 1,000 mg/100 mL | 2,393 | 145 | 6.1% | 86 | 59 |
| IVF - No Additives | 1,398 | 13 | 0.9% | 0 | 13 |
| IVF Fluid (50kg or more) | 1,392 | 145 | 10.4% | 127 | 18 |
| Potassium Chloride 20 mEq/50 mL | 1,107 | 139 | 12.6% | 115 | 24 |
| Antibiotic - Any Volume | 1,025 | 17 | 1.7% | 1 | 16 |
| Phenylephrine 10 mg/250 mL | 827 | 106 | 12.8% | 65 | 41 |

+

Print

**** County General Hospital    1:35 PM    Current User: John Smith    Symbiq Drug Library Compliance: +9% ICU  +6% PE

FIG. 11

Dashboards

Welcome! John Smith
Security Level: Unrestricted
Role: Nursing, Historical
ADVANCED Mode   Logout

| Infusion (Text) | Infusion (Graph-Simple) | Infusion (Graph-Advanced) | ExecScoreCard | Pareto Tables | Rule Set Optimizer | Drug Library Optimizer |

High-level Infuser Information

| CCA Name ▼ | Generic Name ▼ | Display Name ▼ | Medication Amount ▼ | Medication Unit ▼ | Diluent Amount ▼ | Diluent Unit ▼ | Dosi Uni |
|---|---|---|---|---|---|---|---|
| Anesthesia | maintenance IV | Maintenance Fluid | | | 1000 | mL | mL/k |
| Anesthesia | fentanyl | Fentanyl | 50 | mcg | | | mcg/k |
| Anesthesia | heparin | Heparin | 25000 | Units | 500 | mL | Units/ |
| Critical Care | insulin | Insulin | 100 | Units | 100 | mL | Units/ |
| MedSurg | heparin | Heparin | 25000 | Units | 500 | mL | Units/ |
| MedSurg | insulin | Insulin | 100 | Units | 100 | mL | Units/ |
| NICU 1.5 kg | fentanyl | Fentanyl | 250 | mcg | 100 | mL | mcg/k |
| OBGYN | heparin | Heparin | 25000 | Units | 500 | mL | Units/ |
| OBGYN | insulin | Insulin | 100 | Units | 100 | mL | Units/ |
| Oncology | heparin | Heparin | 25000 | Units | 500 | mL | Units/ |
| Oncology | insulin | Insulin | 100 | Units | 100 | mL | Units/ |
| Peds 10 kg | heparin | Heparin | 25000 | Units | 500 | mL | Units/ |
| Peds 10 kg | insulin | Insulin-DKA | 100 | Units | 100 | mL | Units/k |
| Peds 40 kg | heparin | Heparin | 25000 | Units | 500 | mL | Units/ |
| Peds 40 kg | insulin | Insulin-DKA | 100 | Units | 100 | mL | Units/k |
| Telemetry | heparin | Heparin | 25000 | Units | 500 | mL | Units/ |

The table represents Drugs from the Drug Library that are missing information (e.g. limits, overlaps, etc.). Please review each of the listed items.

\*\*\*\* County General Hospital    1:36 PM   Current C

FIG. 13A

Dashboards

Welcome! John Smith
Security Level: Unrestricted
Role: Nursing, Historical
ADVANCED Mode    Logout

| Infusion (Text) | Infusion (Graph-Simple) | Infusion (Graph-Advanced) | Exec ScoreCard | Pareto Tables | Rule Set Optimizer | Drug Library Optimizer |

High-level Infuser Information

Print

| Display Name ▼ | Medication Amount ▼ | Medication Unit ▼ | Diluent Amount ▼ | Diluent Unit ▼ | Dosing Unit ▼ | LHL ▼ | LSL ▼ | USL ▼ | UHL ▼ |
|---|---|---|---|---|---|---|---|---|---|
| anance Fluid | 50 | mg | 1000 | mL | mL/hr | 1 | 5 | 250 | 999 |
| entanyl |  | mcg | 1 | mL | mcg/kg/hr |  | 0.01 | 4 |  |
| Heparin | 25000 | Units | 500 | mL | Units/hr |  | 400 | 2500 |  |
| sulin | 100 | Units | 100 | mL | Units/hr |  | 0.25 | 10 |  |
| sulin | 100 | Units | 500 | mL | Units/hr |  | 0.25 | 16 |  |
| eparin | 25000 | Units | 500 | mL | Units/hr |  | 400 | 2500 |  |
| sulin | 100 | Units | 500 | mL | Units/hr |  | 0.25 | 10 |  |
| entanyl | 250 | mcg | 100 | mL | mcg/kg/hr |  |  |  |  |
| Heparin | 25000 | Units | 500 | mL | Units/hr |  | 400 | 2500 |  |
| Insulin | 100 | Units | 100 | mL | Units/hr |  | 0.25 | 10 |  |
| Heparin | 25000 | Units | 500 | mL | Units/hr |  | 400 | 2500 |  |
| Insulin | 100 | Units | 100 | mL | Units/hr |  | 0.25 | 16 | 20 |
| Heparin | 25000 | Units | 500 | mL | Units/kg/hr |  | 10 | 28 |  |
| ulin-DKA | 100 | Units | 500 | mL | Units/kg/hr |  | 0.02 | 0.12 | 0.2 |
| Heparin | 25000 | Units | 500 | mL | Units/kg/hr |  | 10 | 28 |  |
| ulin-DKA | 100 | Units | 500 | mL | Units/kg/hr |  | 0.02 | 0.12 | 0.2 |
| Heparin | 25000 | Units | 500 | mL | Units/hr |  | 400 | 2500 |  |

The table represents Drugs from the Drug Library that are missing information (e.g. limits, overlaps, etc.). Please review each of the listed items.

nce: +9% ICU | +6% PEDS | -2% L&D | +14% PreOp  PlumA+ Drug Library Compliance: +3% ICU | +1%PEDS | 0% L&D | -2%

SYSTEMS AND METHODS FOR A GRAPHICAL INTERFACE INCLUDING A GRAPHICAL REPRESENTATION OF MEDICAL DATA

CROSS-REFERENCE TO RELATED APPLICATION

The present disclosure claims priority to U.S. Provisional Patent Application No. 61/525,418, filed on Aug. 19, 2011.

FIELD

This disclosure relates to representations and processing of medical data, and more particularly to, examples of graphical and textual displays of medical equipment data and data pertaining to a subject receiving treatment, monitoring or undergoing testing with electronic medical equipment.

BACKGROUND

Individual medical decision support platforms generally function independently without relying on performance optimizations derived from population specific data that is routinely collected. For example, decision support platforms may aggregate information into databases, but generally do not integrate the information or leverage knowledge gained to adapt and optimize therapy management rule sets and parameters to produce enhanced patient safety and patient outcomes.

A dashboard or user interface that adapts to user needs and provides information for treating patients in the presence of comparative analysis data with population performance under similar therapy rule sets and conditions may provide information useful to set alarms on outliers, and to flag outliers to staff for further investigation of inadequate response to therapy, for example.

Thus, an object of the present invention is the provision of a graphical user interface or dashboard system and methods that are useful to users or clinicians at various different levels in one or more healthcare facilities to monitor, manage and improve patient therapy conducted with electronic medical equipment.

This and other objects of the present invention will be apparent from the figures and the description that follows.

SUMMARY

This disclosure may disclose, inter alia, systems and methods for a graphical interface including a graphical representation of medical data such as medical equipment data and data pertaining to a subject receiving treatment, monitoring or undergoing testing with electronic medical equipment. The systems and methods provide real-time, near real-time, and summarized or trended historical information and analysis tools to various levels of interested parties in a healthcare environment.

Any of the methods described herein may be provided in a form of instructions stored on a non-transitory, computer readable medium, that when executed by a computing device, perform functions of the method. In some examples, each function may represent a module, a segment, or a portion of program code, which includes one or more instructions executable by a processor for implementing specific logical functions or steps in the process. The program code may be stored on any type of computer readable medium, for example, such as a storage device including a disk or hard drive. In addition, methods described herein may include one or more operations, functions, or actions that can be performed in a sequential order, performed in parallel, and/or in a different order than those described herein.

Further embodiments may also include articles of manufacture including a tangible computer-readable media that have computer-readable instructions encoded thereon, and the instructions may comprise instructions to perform functions of the methods described herein.

The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage medium.

In addition, circuitry may be provided that is wired to perform logical functions in processes or methods described herein.

In still other examples, functions described herein may be provided within a graphical interface platform. In these examples, the graphical interface platform may include a graphical user interface (GUI). A processor may execute software functions to create a data layout, and additional charts or graphs, on a display device. The display device may be configured to illustrate the graphical user interface, which may be configured to enable a user to analyze medical data in a visual display and accepts user inputs/instructions to illustrate selected data in a desired manner.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 3 illustrates an example screen shot of a configuration of a graphical interface.

FIG. 9 illustrates an example screen shot of data compiled, sorted and ranked in a tabular format.

FIG. 11 illustrates an example screen shot of the interface in FIG. 9 filtered according to a date range.

FIGS. 13A-B are example screen shots of data available under a Rule Set Optimizer tab that shows high-level infuser information, such as drug library information for clinician review.

FIGS. 14-15 illustrate example screen shots of graphical representations indicating real-time and historical information associated with medical devices operating and therapy conditions. The data is filtered, compiled and displayed graphically for clinician review.

DETAILED DESCRIPTION

Figure 1:
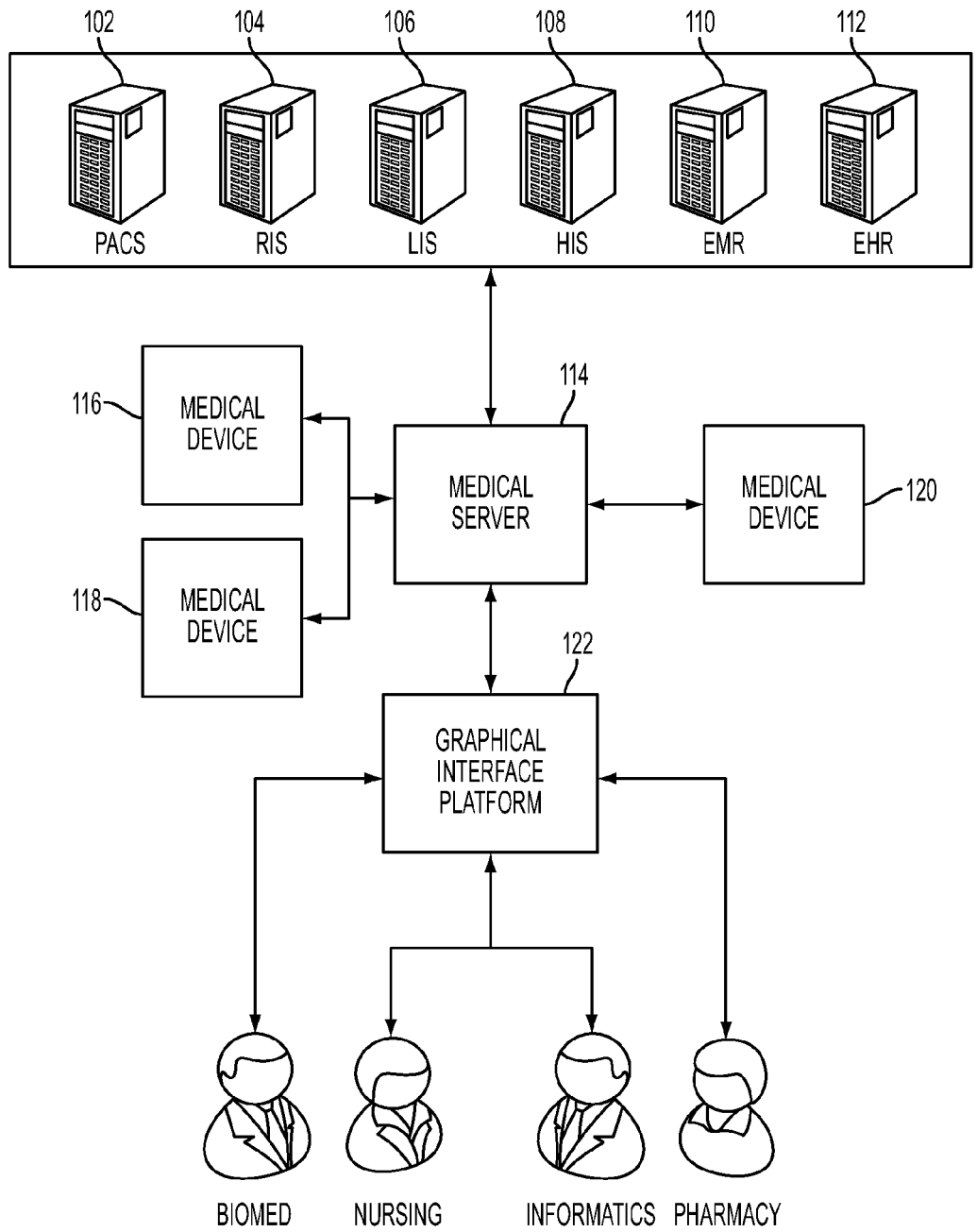
FIG. 1 illustrates an example system for receiving, processing, and providing medical data.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

This disclosure may disclose, inter alia, systems and methods for a graphical interface for providing medical data. The graphical interface may take the form of a graphical user interface (GUI), or of a real-time dashboard (RTD) software platform that is configurable on a user-by-user basis. The interface may be configured to provide contextually relevant data to a user. In some examples, the data may be based on a time frame (reporting intervals), on content (e.g., departments or clinical care areas of a hospital), prior usage patterns, or user type (e.g., pharmacist, nurse, physician, or quality assurance (QA) specialist). A base interval may include "real-time", for example, for a hospital environment in which a clinician may oversee ongoing medication administration. As organizational rank of a user increases, time increments may be expanded to longer (historical) periods of time to provide a higher level summary.

In the context of this disclosure, the terms "real-time", "near real-time" and "historical" are defined in relative terms. Real-time data is essentially current data that has been reported or communicated within about the past five seconds from the medical device, while near real-time data is current data that has been communicated within about the past five minutes, and historical data is previously reported data that was communicated at least about five minutes ago and more typically hours, days or longer ago. Historical data is a fairly easy concept to understand because such data was communicated a considerable time ago and therefore does not accurately reflect the current status of the medical device, nor the medication or patient associated with it. A user can analyze historical data for trends and to understand past activities, occurrences or performance, but would not believe the data to represent a current instantaneous status. However, the distinction between real-time and near real-time data is slipperier, blurrier, much harder to make, and depends greatly on the capabilities of the medical device, the communication network, and the graphical interface platform software to communicate, process, and populate all of the data on a particular graphic user interface screen or dashboard. Thus, the term real-time as used herein should be understood to more broadly include near real-time data as well, even when not specifically stated that way. Real-time data can be used for remote visual monitoring via the graphical interface platform to allow clinicians to locate medical devices, deliver medications to medical devices on a timely basis, and substantially immediately respond to alerts, alarms and other conditions of concern from medical devices or patients connected to the medical devices.

In some examples, the graphical interface platform may receive medical data and provide medical safety reporting capabilities including reporting of history data and real-time visual monitoring data. The graphical interface may be provided through an Internet or intranet interface, and can be made available to users on a restricted access basis.

In further examples, the graphical interface platform may be configured to identify potential problems and corrections to medical devices in operation while a reporting cycle is underway through visual representation of performance metrics.

The graphical interface platform may be a web-based user-by-user configurable real-time visual monitoring platform that provides contextually relevant and actionable data to the user. User adjustable filters can be provided to give the user an ability to drill down to identify potential actionable corrections as a result of alarms, alerts, infusion pump status, hard/soft limit overrides. Features include rules and/or algorithm engine, reporting, charting, drug library optimizer, and data aggregation of $3^{rd}$ party HIT data sources, and dashboard settings, user access and privileges can be determined based on area of use (e.g., nursing, pharmacy, or biomed).

Referring now to the figures, FIG. 1 illustrates an example system for receiving, processing, and providing medical data. The system includes a number of servers, such as a picture archiving and communication system (PACS) 102, a radiology information system (RIS) 104, a medical list server (LIS) 106, a hospital information system (HIS) 108, electronic medical records (EMR) 110, and electronic health records (EHR) 112, for example, that are coupled to a further medical server 114. The medical server 114 may further be coupled to a number of medical devices 116, 118, and 120, which may include any number of devices like infusion pumps, monitors, bedside computers, etc. The medical server 114 may be configured to receive information from the number of servers and medical devices, and provide the information to a graphical interface platform 122. Any number of users/clinicians, including without limitation nurses, doctors, hospital administrators, etc., who have different data needs, may access the graphical interface platform 122, and information provided on the graphical interface platform 122 can be configured accordingly.

The medical server 114 may process received information in a number of ways, and thus, may provide a number of functions including localized monitoring and control for hospital-created clinical care areas (CCAs), specific drug libraries and dosing recommendations based on hospital guidelines and industry best practices, determine hard and soft dosing limits to provide medication safety at the bedside for clinicians, allowing them to practice according to established best practices while allowing flexibility and adjustment for special patient populations as needed. In addition, within hospital-created guidelines, real-time monitoring of medication administration at the bedside, and real-time verification of the "5-Rights" may be provided. In one example, the medical server 114 may include or be configured to operate according to the Hospira MedNet™ server suite software, provided by Hospira of Lake Forest, Ill.

The graphical interface platform 122 may be configured to present centralized (server-based) medical device data (e.g., infusion pump data) to provide actionable data for continuous quality improvement (CQI) purposes to increase medication safety at the bedside and potentially reduce or avoid ADE's (adverse drug events). An example for such actionable data is referred to herein as an Executive Scorecard. Executive scorecards allow the clinicians (administration or medication safety committee) to view the highlights of past medication administration ("top ten" in different categories). Viewing these data highlights provides the clinician the ability to investigate and target medications causing the most problems (such as the most alerts, edits and overrides) for the clinicians or patients at the bedside. The success of resulting changes and adjustments to clinical practice can be monitored on an ongoing basis by reviewing the Executive Scorecard data. The graphical interface platform 122 may configure data to report occurrences when safety software is not being used and/or an alarm or alert is triggered (allowing for real-time intervention by the clinician at the bedside), identify alarm, alert or limit overrides, identify trends in clinical practice (how doctors are prescribing medications and how nurses are administering them), configure and optimize a "drug library" and rule sets that govern acceptable parameters related to a given medication/concentration in a specific clinical care area or CCA, or provide decision support/optimization tools for "smart" IV pumps. The graphical interface platform 122 also provides the ability for the clinician to perform ad hoc data analysis with the "drill-down" capability of the interface.

The graphical interface platform 122 may provide a Local Clinical Decision Support System (LDSS), which may provide information for advanced management of therapy with optional event alerting and notification and automation of decisions (e.g., therapy modification or suspension). For example, a probabilistic model, including Bayesian Decision Trees, may be employed, based upon prior population data, to identify specific adverse drug events, such as hypoglycemia. The graphical interface platform 122 may provide a dashboard of information that displays information on population behavior of patients with similar classifications or undergoing similar clinical therapies by presenting population summaries and comparing individual patients with relevant population outcomes. The dashboard may allow population comparative analysis to refine local decision support performance or produce alarms/alerts that are meaningful with respect to indicating population outliers. Information can be presented in real-time and may be relevant to current therapies administration. Furthermore, dashboards can also be used to monitor measured diagnostics, therapy outcomes, and decisions of multiple therapies decision support systems for the same patient.

The medical server 114 may provide access to the graphical interface platform 122 in real-time and via a web-interface. The graphical interface platform 122 may monitor a patient from a perspective of applied therapy, and may further represent inputs (medication infusion), outputs (physiological response), and medication sensitivity in a graphical manner. As a result, clinicians can view results of therapeutic decisions in real-time and identify individuals whose states are improving or degrading.

Information provided by the graphical interface platform 122 may be representative of information from Enterprise Clinical Decision Support Systems (EDSS) that can collect and further analyze information generated by Local Clinical Decision Support Systems (LDSS), such as glucose management or coagulation management. The EDSS can leverage knowledge of patient population performance under various therapy protocols to optimize the therapy rule sets and/or probabilistic models of local decision support systems. Patient population subgroups can be determined from patients with similar classifications using multiple parameters or characteristic of that population, for example, age, height, gender, weight, ethnicity, risk profile and clinical indication.

Therapy rule sets and algorithms that adapt therapy initialization using population specific information can be optimized using information derived from databases representing the patient population with relevant classification. Therapy initialization parameters include dose volume, boluses, starting infusion rates, timing of diagnostics measurements and patient specific information (e.g., demographics, medication allergies, lab values, and therapy histories).

The graphical interface platform 122 can provide predictive capabilities based on statistical sampling, clinical modeling and trend analysis. Comparative analysis can be made between a specific patient performance under a therapy protocol and remaining patient population subgroup on the same protocol, and alarms or alerts can indicate if this patient is an outlier from the general population that was treated under similar conditions and protocols. Statistical tools used to indicate outliers include box-car plots, decision trees, probabilistic models, cluster analysis, and abstract factor analysis, for example. Outlier patients may simply be part of a special patient population or may indicate a medication contraindication, or an interaction between multiple medications preventing the therapy protocol from achieving its expected effectiveness. Patient and population information can be presented in real-time and may be relevant to current therapies administrated. Speed to response is critical in some therapy protocols, allowing for real-time intervention at the bedside, preventing ADE's, patient harm and potentially saving lives.

Quality metrics can be provided and may be indicative of effectiveness of the adopted therapy protocols and safety metrics can also be collected to ensure therapy protocols are also safe.

Compliance metrics can also be collected and assess clinical practice and adherence to established "best practice" therapy protocols; preventing adverse outcomes and ADE's. Process control metrics such as six-sigma P-charts can be provided and may be indicative of how reproducible the desired measured outcomes are, and deviations from expected targets and acceptable ranges may indicate need for quality initiatives.

In some examples, the graphical interface platform 122 enables integration of information from multiple sources relevant to multiple therapies administered on the same patient such as therapy outcomes, medication allergies, medication history, orders, decisions, diagnostic lab values, vitals, etc., to allow for comprehensive dashboards to monitor and diagnose overall patient status and coordinate interaction between individual therapy protocols administered for more informed decision making. Coordinating multiple LDSS may produce managed and synchronized decisions to prevent undesired interactions and adverse events, optimize therapy decisions and allow for integration and documentation of information on sources of variability to an expected outcome of a particular LDSS.

Dashboards can further function to integrate information from multiple data sources, across heterogeneous hospital networks and information systems, and may aggregate and normalize databases and information, for example, such as combining multiple allergy definitions and vocabulary into a single standard definition (e.g., since medical terminology and uses are predominantly not standardized). A reference vocabulary database can be used along with a natural language processing engine to determine a context of use of terminology and eligibility for substitution, and the dashboard may automate selection of an appropriate reference vocabulary.

Dashboards can be further used to measure frequency of alerts, and alert loading per clinician, as well as workload per clinician, and average length of stay for patients as measures of quality of care. Other quality metrics can be designed to provide close to real-time monitoring of quality of operations. As an example, the dashboard may provide a patient event monitor that generates an alert when a change in patient condition has been detected on a basis of estimated internal control parameters (e.g., estimated medication sensitivity, compartmental volumes, and opioid efficacy). In some examples, the dashboard provides a model of the patient and detects a change in a condition of the patient on the basis of estimated internal parameters rather than observed measurements (e.g., vitals and labs).

In some examples, the graphical interface platform 122 may be configured to process information exchange between a plurality of local devices performing local decision support, and may benefit from population aggregated data to produce optimizations to the local decision support as well as indicate comparatively outliers from mainstream population outcomes as early alarms for need for intervention.

Figure 2:
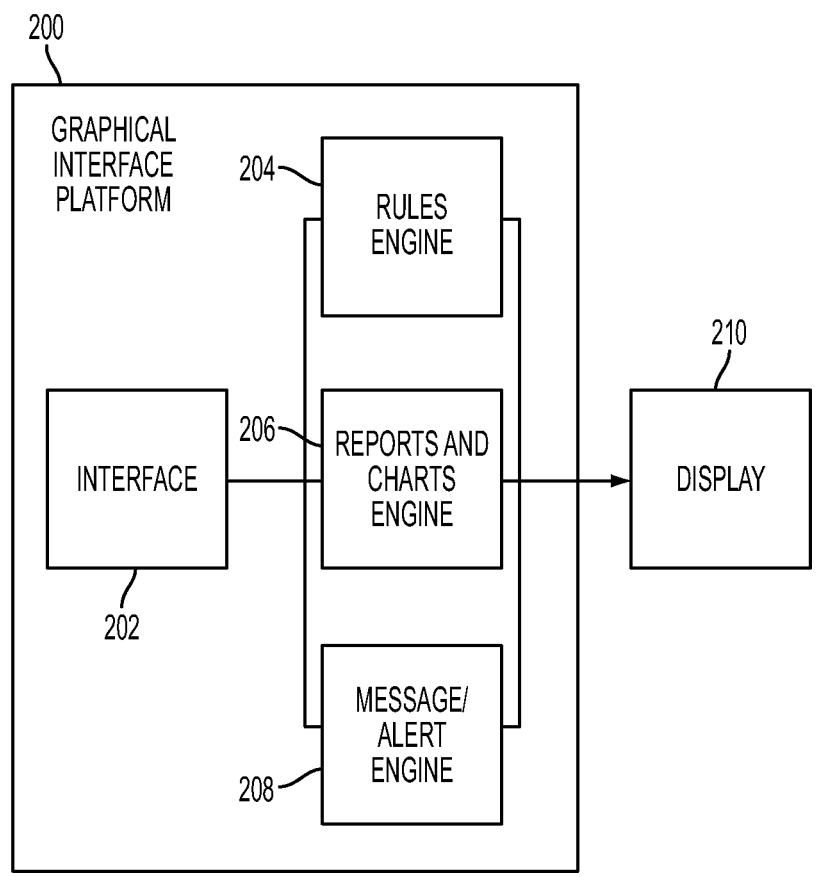
FIG. 2 is a block diagram of an example graphical interface platform.

FIG. 2 is a block diagram of an example graphical interface platform 200. The graphical interface platform 200 includes an interface 202, a rules engine 204, a reports and charts engine 206, a message/alert engine 208, and is coupled to a display 210.

The interface 202 may be a web-based interface enabling access by users via the Internet or intranet. Information provided to the display 210 may be based on a role-based view to enable context-relevant details (e.g., by discipline and detail level), and may provide user-specified customization of displayed data in a view.

The rules engine 204 may be configured to generate actionable notifications based on user-defined thresholds or internal decision models (e.g., decision trees, artificial neural network, Markov model, probabilistic networks, etc.) and route them to the user's preferred communication device (e.g., pager, cell phone, PDA, workstation, etc.). The reports and charting engine 206 may be configured to run ad hoc reports based on user-defined preferences. The message/alert engine 208 may be configured to route actionable notifications by email, pager, mobile phone, SMS, nurse station, central operator, etc., based on user preferences.

The graphical interface platform 200 may provide real-time visual monitoring of safety and operational metrics, real-time alerts that are pushed out to clinicians to enable immediate response, and trending/early warning indicators to identify opportunities for improvement. Information that is provided to the display 210 can be filtered based on a user customization, such as for nursing, pharmacy, biomed, risk management/quality, information technology, etc. Data from a number of servers (e.g., shown in FIG. 1) can be consolidated to provide patient-pump-caregiver visibility (for example from a barcode point of care or BPOC server), real-time location of pumps in facility (for example from a real-time location system or RTLS server), pump utilization and inventory versus hospital census (for example from an admissions-discharge-transfer system or ADT server), pumps requiring preventive maintenance (PM) or corrective action (computerized maintenance management system (CMMS), etc.

Furthermore, data may be output in a form of executive scorecards to allow c-level (Chief Information Officer, Chief Executive Officer, Chief Nursing Officer, etc.) hospital leaders to review actionable data, assess and leverage metrics and understand hospital performance as related to medication safety. Hospitals may produce scorecards "on-the-fly" to identify clinical trends in medication administration, deviations from established "best practices"—providing the needed focus for corrective interventions, assessing the effectiveness of such interventions in an effort to improve medication safety at the bedside and prevent ADE's and potential patient harm.

Each of the rules engine 204, the reports and charts engine 206, and the message/alert engine 208 may receive a set of parameters related to therapy objectives for a patient and thresholds for all input/output and calculated variables. Each of the rules engine 204, the reports and charts engine 206, and the message/alert engine 208 may include an input module that receives the infusion information and diagnostic response, a calculation module that models the input/output or I/O relationship between the medication infusion and diagnostic response, a database for accumulating calculated parameters specific to the calculation module, a decision module that monitors inputs, outputs and calculated parameters and detects changes in any or all of the three categories, and an alert capability that is set when a change has occurred.

The calculation module may include a single multivariate model, such as used with time varying parameters or probabilistic network, that are adjusted based upon data and clinician input using maximum likelihood optimization, structured optimization (e.g., genetic or hill-climbing algorithms), an extended Kalman filter, Bayesian estimator based upon input/output data. The calculation module may also include a mixture of single models operating in parallel. The individual models are weighted or prioritized based upon prediction error. In addition the models can be used for prediction and analysis of possible outcomes. The calculation module may further include other multiple models, in which a group of static models can be used to identify patient responses and the group of models with a lowest prediction error through time can be selected for analysis.

The graphical interface platform 200 may be configured to model patient therapy and response dynamics and detect a change in condition of the patient on the basis of internal parameters. The rules engine 204, the reports and charts engine 206, and the message/alert engine 208 may provide predictions of future physiological variables and risk metrics for display on the dashboard. The graphical interface platform 200 may be further configured to model therapy alternatives and select an objective that best suits the therapy objective. Therapy objectives can be selected based on time to reach targets or safety, such as avoiding medication interactions, optimizing medication delivery profiles, minimizing the risk of an adverse outcome or reducing cost of therapy.

The graphical interface platform 200 may be configured to operate on a computing device. Alternatively, a computing device may be configured to provide the graphical interface platform 200. The computing device may be a personal computer, mobile device, cellular phone, tablet computer, etc., and may be implemented to provide the graphical interface platform including a graphical representation as shown in any of FIGS. 3-15 described below. In one configuration, a computing device may include one or more processors and system memory that includes one or more applications and program data. The computing device may be configured to execute instructions to perform functions of the graphical interface platform. The instructions may be implemented as computer program instructions encoded on a non-transitory computer-readable storage media in a machine-readable format, or on other non-transitory media or articles of manufacture.

FIGS. 3-15 illustrate example screen shots of a graphical interface platform as a dashboard program. In these examples, the graphical interface platform is provided as a graphical user interface (GUI). Thus, a processor may execute software functions to create a data layout, and additional charts or graphs, on a display device. The display device 210 (FIG. 2) illustrates the graphical user interface, which enables a user to analyze medical data in a visual display and accepts user inputs/instructions to illustrate selected data in a desired manner. The graphical user interface (GUI) may be of a standard type of user interface allowing a user to interact with a computer that employs graphical images in addition to text to represent information and actions available to the user. Actions may be performed through direct manipulation of graphical elements, which include windows, buttons, menus, and scroll bars, for example.

A user name and password may be required to access the dashboard program. If the password or user is not recognized based on a database of eligible users, the user cannot continue to the next screen. Based on the user identification numbers, users can be assigned various privileges and rights, which allow access to view various data with various granularities. For example, based on organizational hierarchy, levels and qualifications of the user (e.g., bedside nurse versus facility supervisor/charge nurse versus Chief Nursing Office or CNO versus Pharmacist), different types and details of relevant information may be shown. The type and amount of information may be customizable per user, user type, or privilege status.

The example screen shots in FIGS. 3-15 illustrate medical data pertaining to infusion pumps; however, the medical data may be related to or received from any number of other medical devices.

FIG. 3 illustrates an example screen shot of a configuration of the dashboard. The dashboard includes many tabs such as: Infusion (Text), Infusion (Graph-Simple), Infusion (Graph-Advanced), ExecScoreCard, Pareto Tables, Rule Set Optimizer, Drug Library Optimizer. Data of the first tab ("Infusion (Text)") is illustrated in FIG. 3 displaying text-based "High-level Infuser Information", such as "CCA", device type or name ("Pump Name"), Drug Library compliance or usage ("DL in use"), "Alert Status", "Alarm Status", high-risk medication indication ("High-risk Med"), and "Power Status" by way of example and not limitation. In addition, the dashboard provides "Infuser Location and Infusion Therapy Information" including but not limited to infuser "Asset No." as shown and "Location" (not shown), as well as infusion therapy information such as Pump Name, "Medication", "Concentration", "Dose", "Rate", programmed volume to be infused ("VTBI"), "Volume Remaining" in the container or of the programmed VTBI, "Rule Sets" that are being employed, etc. A user may scan through all pumps that are online and infusing, view real-time alerts/alarms or power status. The data in the Alert Status and Alarm Status cells provide immediate information and feedback to the clinician, allowing for real-time decision making and prioritization. Filters can be applied to include or exclude certain devices, events or specific criteria. Alerts are typically informative in nature, whereas alarms can indicate situations requiring immediate intervention to not delay therapy, i.e., a distal occlusion caused the device to alarm and stop the infusion. Flashing text, special symbols, or colors such as red, yellow, orange, etc. can be used to better draw the user's attention to alarms or alerts if the status is something other than "none".

The delivery of high-risk medications is specifically shown and/or highlighted on the dashboard to allow for greater focus when monitoring medication administration for a whole unit or clinical care area. The power status indicates if the pump is currently powered by a battery or A/C power source, and the current amount of power or battery capacity remaining, which can be expressed as a percentage. If the pump is currently plugged into an A/C power source, a default value of 100% is displayed for power status, but the actual remaining capacity of the battery while it is recharging can be displayed alternatively or in addition thereto. The data shown on this page may be received from Hospira MedNet™ software. The user may print this screen to a printer using the "Print" button shown in the upper right corner area of the screen. The display of the infuser location is pertinent in tracking devices for purposes of recall, maintenance, installation, Drug Library update, etc. The infuser location may be useful for dispensing and delivering an additional full IV bag to a proper pump. For example, a pharmacy may dispense another bag and deliver it to the correct location.

Figure 4:
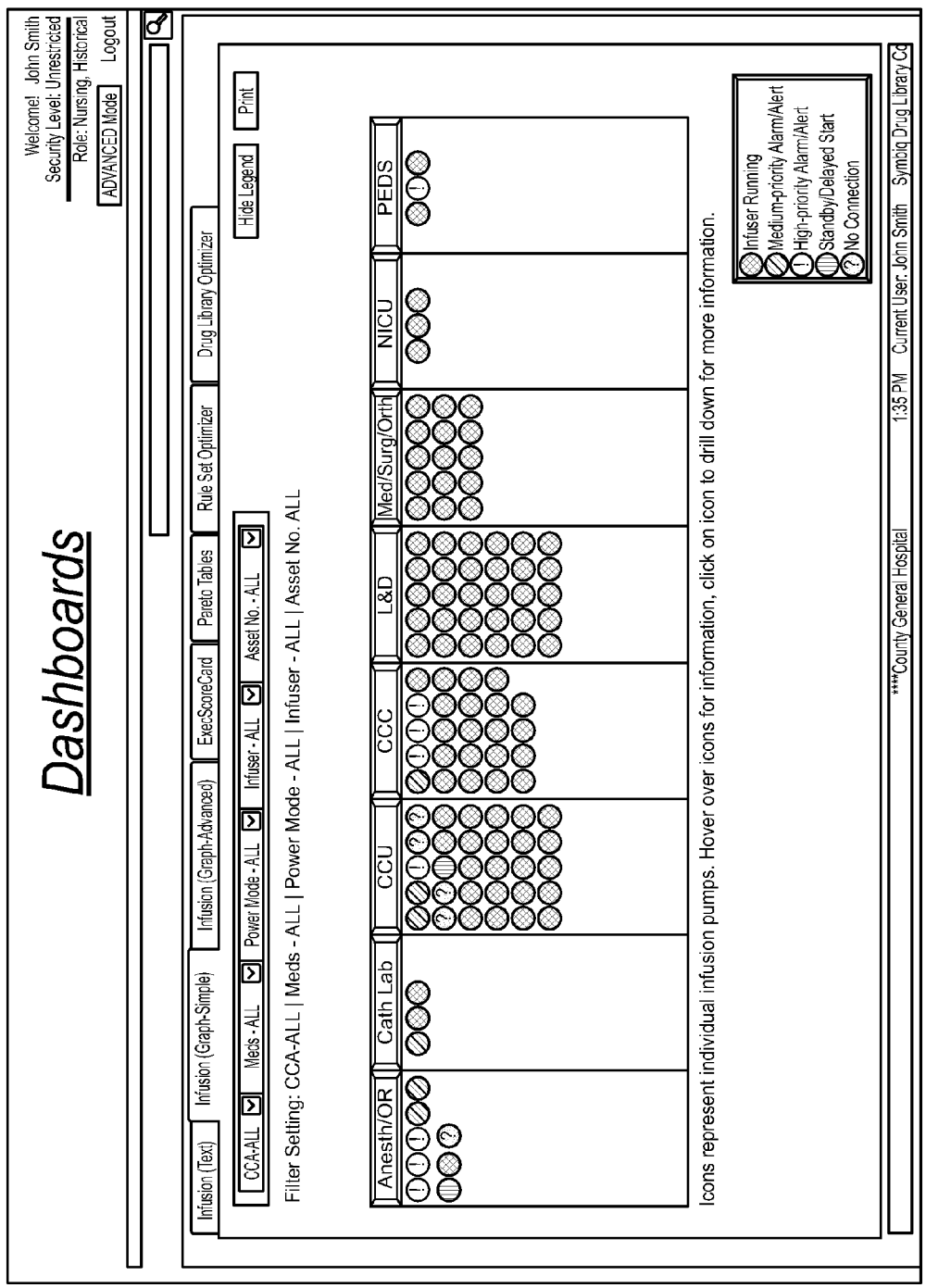
FIG. 4 illustrates an example screen shot of data in a graphical interface in a Graph-Simple form.

In addition, the graphical interface may associate a medical device to a patient based on a location of the medical device and/or based on a location of the patient. An example screen shot of data of the second tab ("Infusion (Graph-Simple)") is shown in FIG. 4. Each icon in the illustration may represent a medical device (e.g., an infusion pump). The icon shown in the example of FIG. 4 is a circular dot that may be filled in with certain colors, symbols, and text or display characteristics. A circular dot is beneficial in that a great number of distinct medical devices or pumps can be clearly shown for one or more clinical care areas in a small amount of space on the screen. However, other icons with different shapes, colors, and text and display characteristics can be utilized without detracting from the invention. The icon could be an actual image of an infusion pump system or a simplified pictorial representation of key aspects of the pump system such as the battery or power bus, container(s) the pump is drawing from, patient the pump is connected to, etc. See FIGS. 7 and 8 for examples of simplified pictorial representations of a plurality of pumping systems on the dashboard. Referring again to FIG. 4, the colors and symbols on the dots convey information about a status of the infuser (e.g., green if infuser is running, yellow if there is a medium-priority alarm/alert, red with an optional exclamation point inside if there is a high-priority alarm/alert, blue if the infuser is on a standby or delayed start, or gray with an optional question mark inside if the infuser is offline or not connected to the network, etc.). The representations of the colors and symbols can be included in a legend at a bottom of the dashboard screen, as illustrated in FIG. 4. Each column may represent an area in a hospital, which may be filtered using a pull-down menu by a user. Further filters are provided to filter pumps to be displayed by area, medication type in general or medication type by category (high-risk or low-risk, antibiotics, etc.), power mode (infuser running on batteries or A/C), types of infuser (e.g., PLUM A+™, SYMBIQ™, LIFECARE PCA™, SMITHS MEDICAL MEDFUSION™, ALARIS MEDLEY™, B. BRAUN OUTLOOK™, SIGMA™, etc.), and Asset No. (and/or serial number, MAC address, IP address, wired or wireless access node, etc.).

Figure 5:
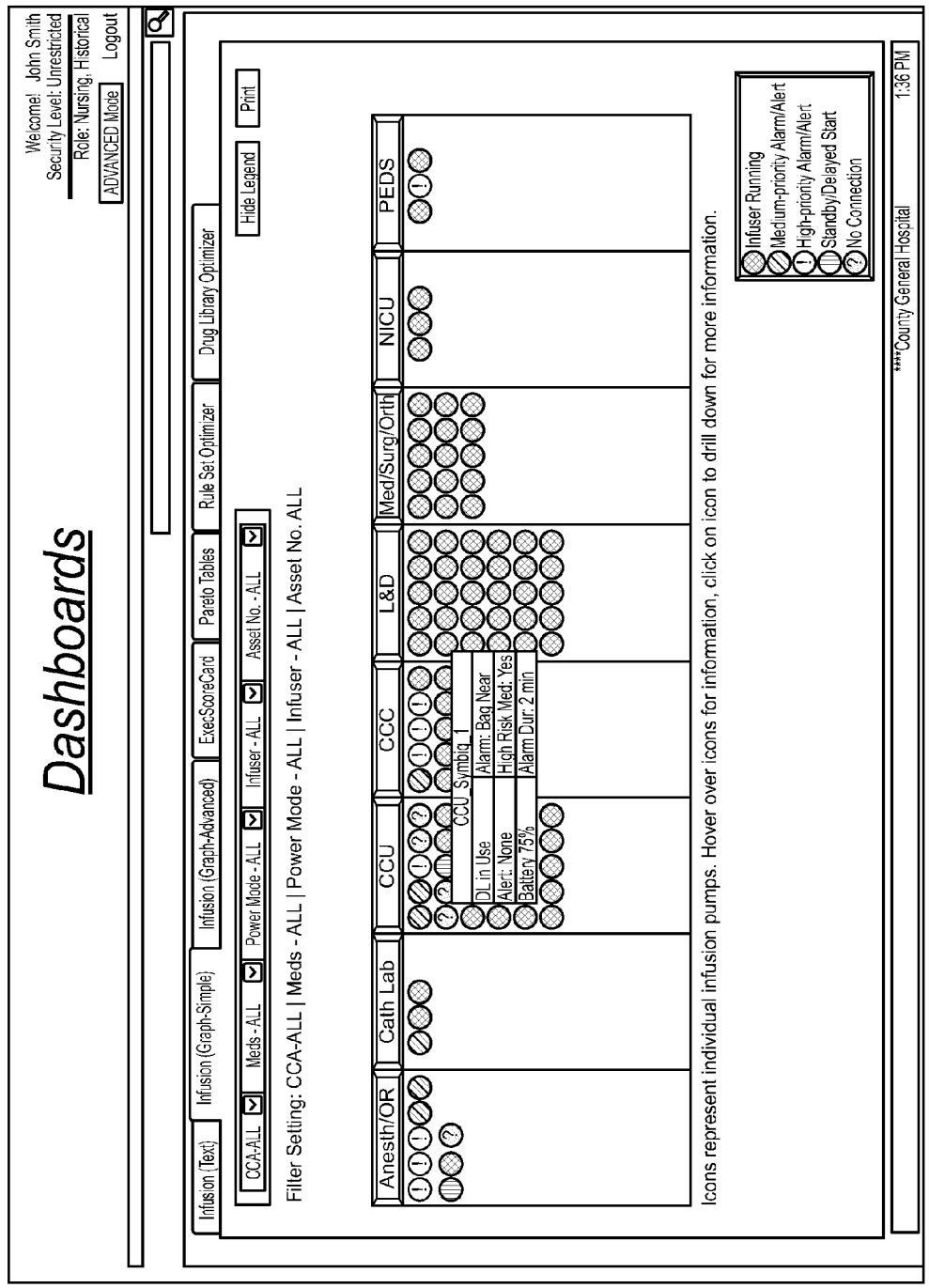
FIGS. 5-6 illustrate an example screen shot of the graphical interface shown in FIG. 4 with additional associated information.
Figure 6:
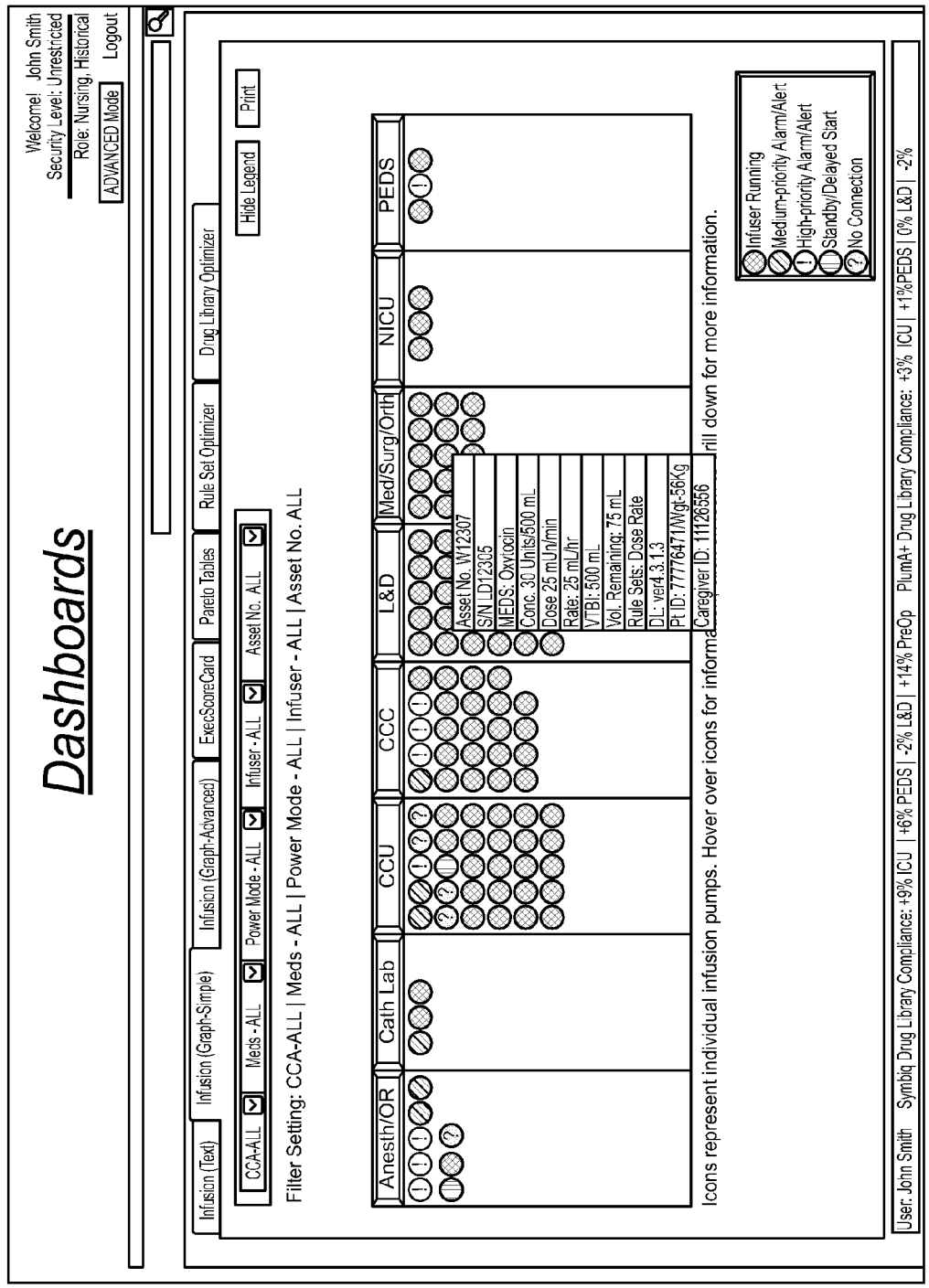

Using a cursor or pointer device, hovering over a dot may provide additional information, such as shown in FIGS. 5-6, including a pump's current status, ID, caregiver ID, etc. For example, a user may hover-over an icon to cause the graphical representation to produce a pop-up screen containing more specific information on the medical device including infuser name, whether the drug library is in use, alert status, battery life, alarm status (here an IV container or bag the pump is drawing from is nearly empty), whether the infuser is infusing a high-risk medication, if there was an alarm/alert and length of time the incident has gone unresolved, etc. As seen in FIG. 6, for example, using a mouse, a user may click-down on an icon to cause the graphical user interface to search for more information on the medical device including asset number, serial number, medication, concentration, dose, rate, volume to be infused (VTBI), volume remaining, rules sets, drug library, patient identification number, caregiver information, etc.

Figure 7:
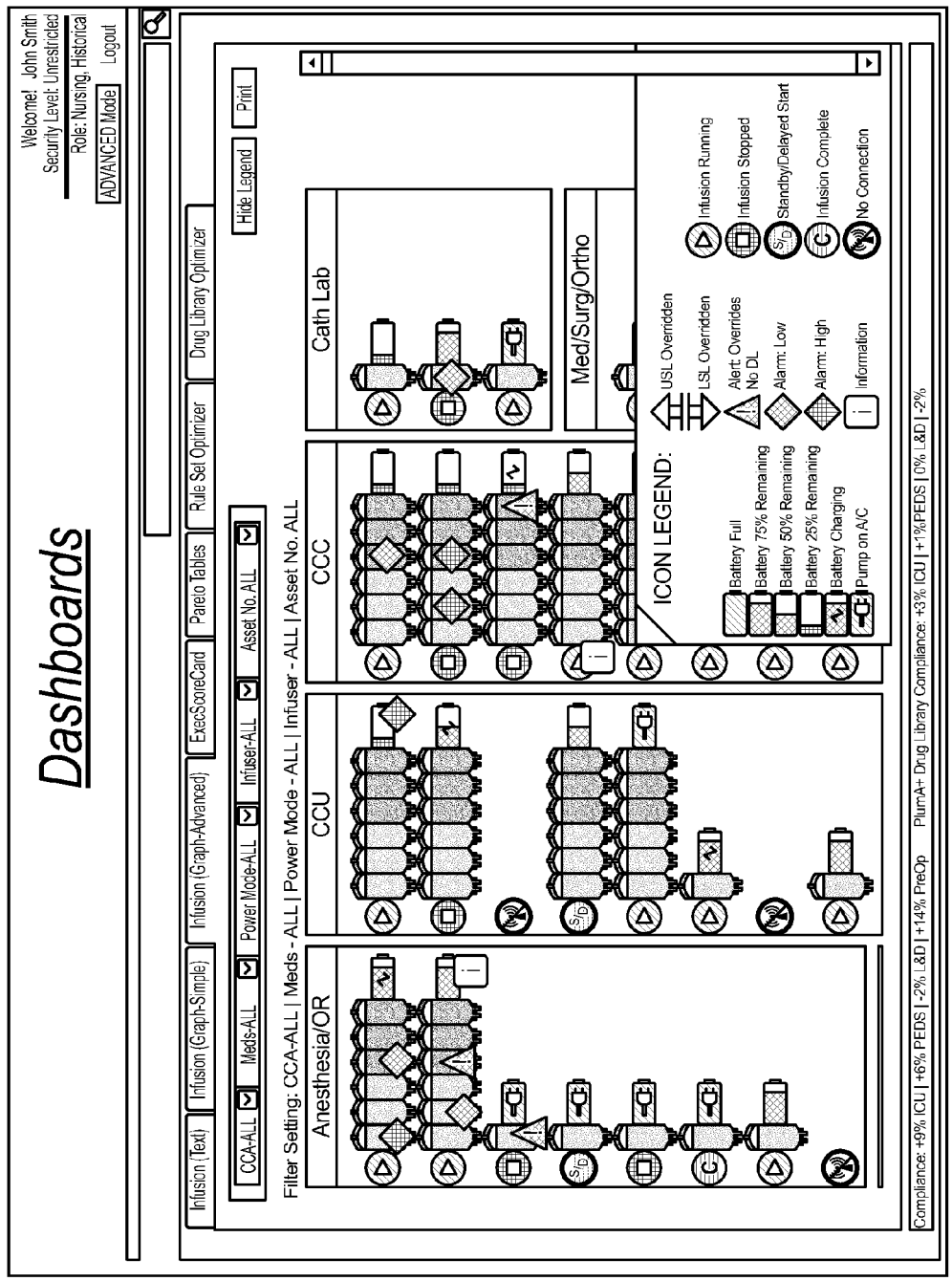
FIG. 7 illustrates an example screen shot of data in a graphical interface in a more detailed "drilled down" graphical format.

An example screen shot of the "Infusion (Graph-Advanced)" tab is shown in FIG. 7. Data illustrated on this page may be filtered in the same manner as previously described. Each line or horizontal section in the illustration may graphically represent an infusion pump (or single infuser), and each column in the illustration may graphically represent a clinical care area or CCA. Alternatively each line of the illustration may represent a multi-channel infusion pump system that includes a plurality of infusers or infusion channels associated with a common support structure or patient. Information contained graphically for each infuser on the horizontal lines include infuser status (e.g., a green dot with optional white, right-facing triangle inside for an infusion running, a red dot with optional square inside for infusion stopped, a red outlined circle with optional gray fill and white "S/D" text inside for standby/delayed start, a blue dot with an optional white "C" inside for infusion complete, and a red outlined dot with an optional diagonal red backslash striking through a wireless symbol for infuser offline or no connection), notification (e.g., a yellow triangle with an optional exclamation point inside for an alert such as no drug library present or in use (this is sometimes referred to as drug library "compliance"), a yellow up arrow indicates that the operator has overridden an upper soft limit, a yellow down arrow indicates that the operator has overridden a lower soft limit, or pump operator, a yellow diamond for low concern or priority alarms, a red diamond for high concern or priority alarms, and a white square with an optional "i" inside for general information), and power status (e.g., battery images colored and shaded or proportionally filled so as to depict battery conditions such as battery full (100% green), battery 75% remaining (75% yellow), battery 50% remaining (50% yellow), battery 25% remaining (25% red), a battery image with a charging symbol inside to indicate the battery is charging, a battery image with a symbol or picture of an A/C plug inside to indicate the pump or infuser is operating on A/C).

Each line-item representation of an infuser under a specific clinical care area indicates in real-time the current status of the pump, container information, and battery information. A number of bag/container icons are used to indicate how many containers are being administered by the infusion pump. By way of example, for a three-channel infusion pump system that can deliver from two containers per channel in an alternating sequence or simultaneously, up to six total bags/containers are shown in FIG. 7 to graphically illustrate pump-status, alarms, alerts, container status, etc. Thus, infusion pumps with single pumping channels or pumps with multiple pumping channels can be illustrated. Information from infusion pump systems including single or multiple channel infusion pumps in combination with other medical devices can be illustrated as well. For example, a pump and a physiological monitor or meter such as a pulse oximeter (SpO2), capnography (ETCO2) meter or glucometer can be included in the pump system and illustrated by the dashboard. When multiple containers are ordered for the patient, a graphic depiction or icon of a container in waiting can be provided above, below, or partially behind the icon for container in use. The user can filter the information based on: clinical care area, medication type (high-risk or low-risk), power mode (infuser running on batteries or A/C), infuser type (e.g., PLUM A+™, SYMBIQ™, LIFECARE PCA™, SMITHS MEDICAL MEDFUSION™, ALARIS MEDLEY™, B. BRAUN OUTLOOK™, SIGMA™, etc.), and Asset No. (or serial number, MAC address, IP address, wired or wireless access node, etc.). Data illustrated in FIG. 7 is provided using graphical icons to enable an easy to use, quick, visual, intuitive illustration of the data for a user.

Figure 8:
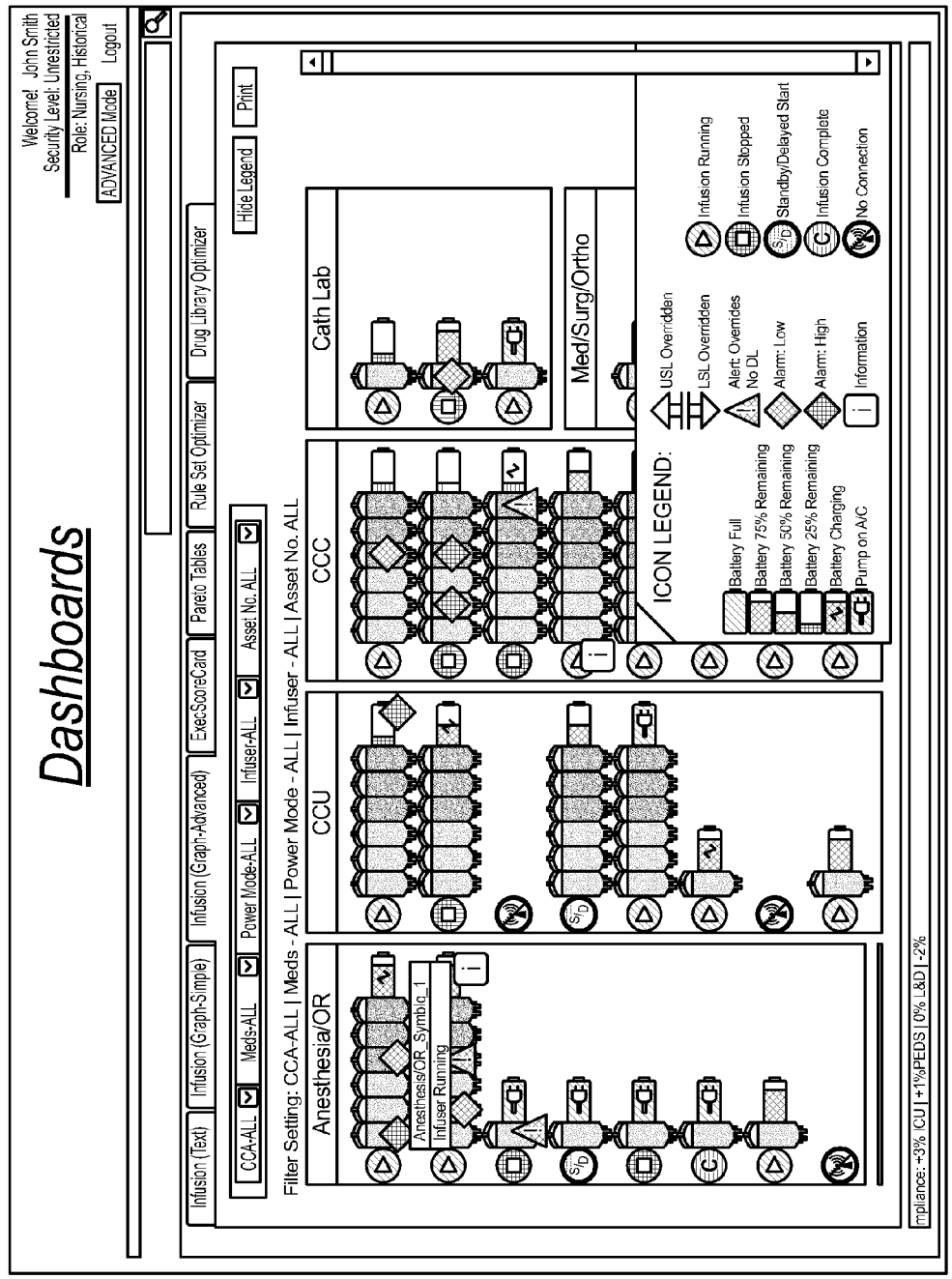
FIG. 8 illustrates an example screen shot of the graphical interface shown in FIG. 7 with additional associated information.
Figure 10:
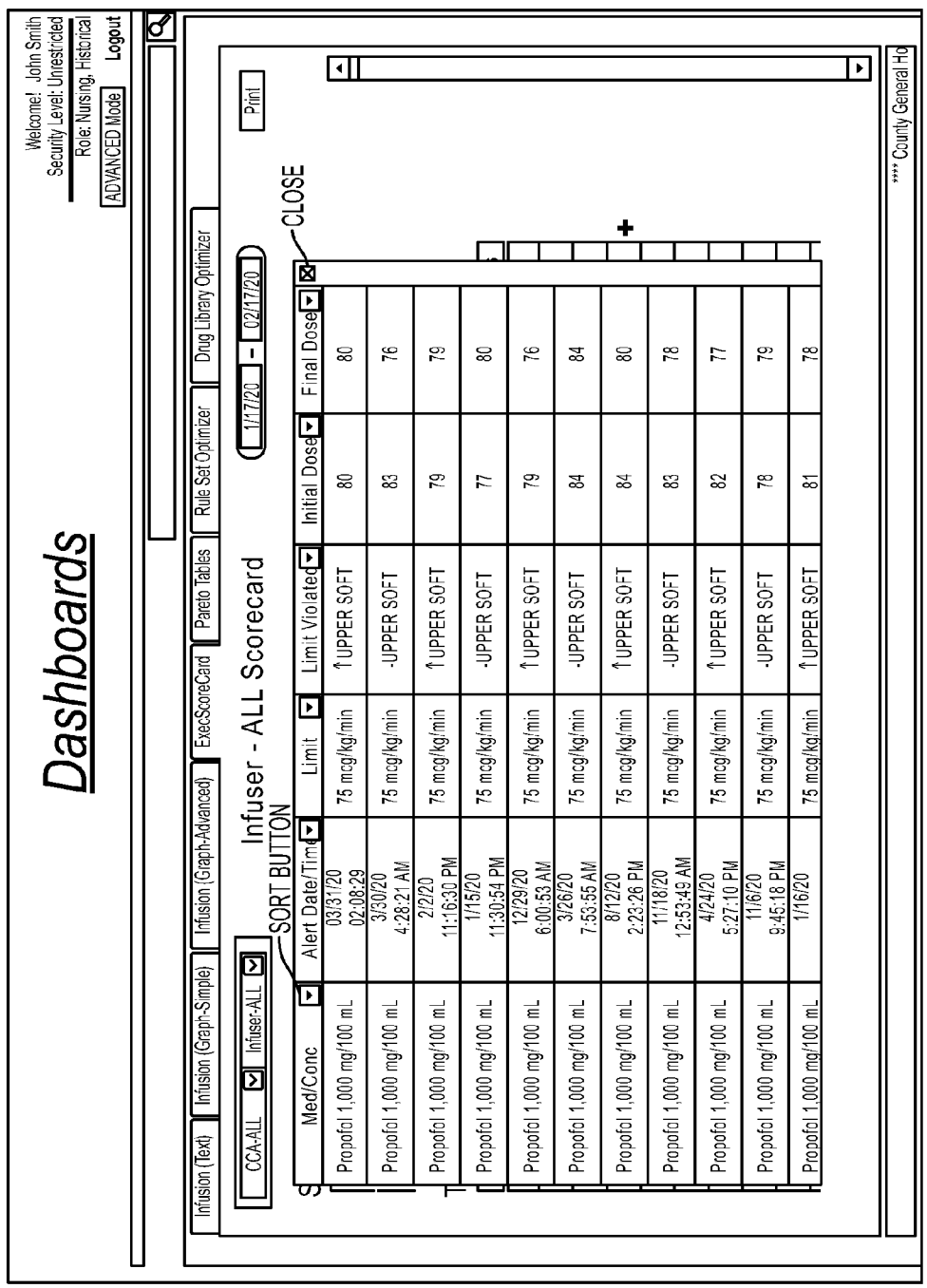
FIG. 10 illustrates an example screen shot of detailed "drill down" information associated with the interface in FIG. 9.

Using a pointer device, hovering over any of the icons in FIG. 7 may provide additional real-time information, such as shown in FIG. 8. Hovering over an icon causes the graphical representation to produce a pop-up screen containing more specific information on the infuser, the wired or wireless network, the medication order, the medication in the container, or the patient.

An example screen shot of the ExecScoreCard tab is shown in FIG. 9. Data in this interface is more historical in nature and may be filtered per time period, per infusion pump, or per clinical care area. The dashboard may generate the executive scorecard data from the raw Hospira MedNet™ database. The executive scorecard produces actionable, sorted data providing focus in identifying medication delivery trends and clinical best practice variations and potential issues. Categories are displayed in "Top 10" format and include medications causing the most alerts overall, medications causing the most overrides, edits and medications causing the most hard limit alerts. The example shown in FIG. 9 displays a summary at the top for all CCAs and all infusers for a selected period of time, which includes but is not limited to Drug Library compliance, total number of programs, total number of alerts, overrides, edits, etc. The example then displays the "Top 10" medications causing alerts; summarizing total programs, alerts, % of alerts to programs, number of overrides and number of edits. If a user would like to investigate a specific medication (in our example Propofol), clicking on the red "+" allows the clinician to view the data related to Propofol down to the individual program and infusion level. The result of this "drill down" is illustrated as a pop-up overlay in FIG. 10. The user can view each individual program involving the chosen medication (in our example, Propofol), including alert date and time, the type of limit violated, the numeric value of the limit as well as the initial and final dose entered by the clinician on the infusion device. Filters allow a user to focus and narrow metrics, namely the filters include: clinical care area, infuser type (e.g., all, PLUM A+™, SYMBIQ™, LIFECARE PCA™, SMITHS MEDICAL MEDFUSION™, ALARIS MEDLEY™, B. BRAUN OUTLOOK™, SIGMA™, etc.), and a date-range of the report. FIG. 11 is an example screen shot to filter the data by a date-range. Sorting buttons are provided at the top of each column of data in FIG. 11 to allow the user to sort the data displayed alphabetically, alphanumerically or numerically, if desired. It will be appreciated that such sorting buttons are contemplated to be used on other tables of data shown in the figures and discussed herein.

Figure 12:
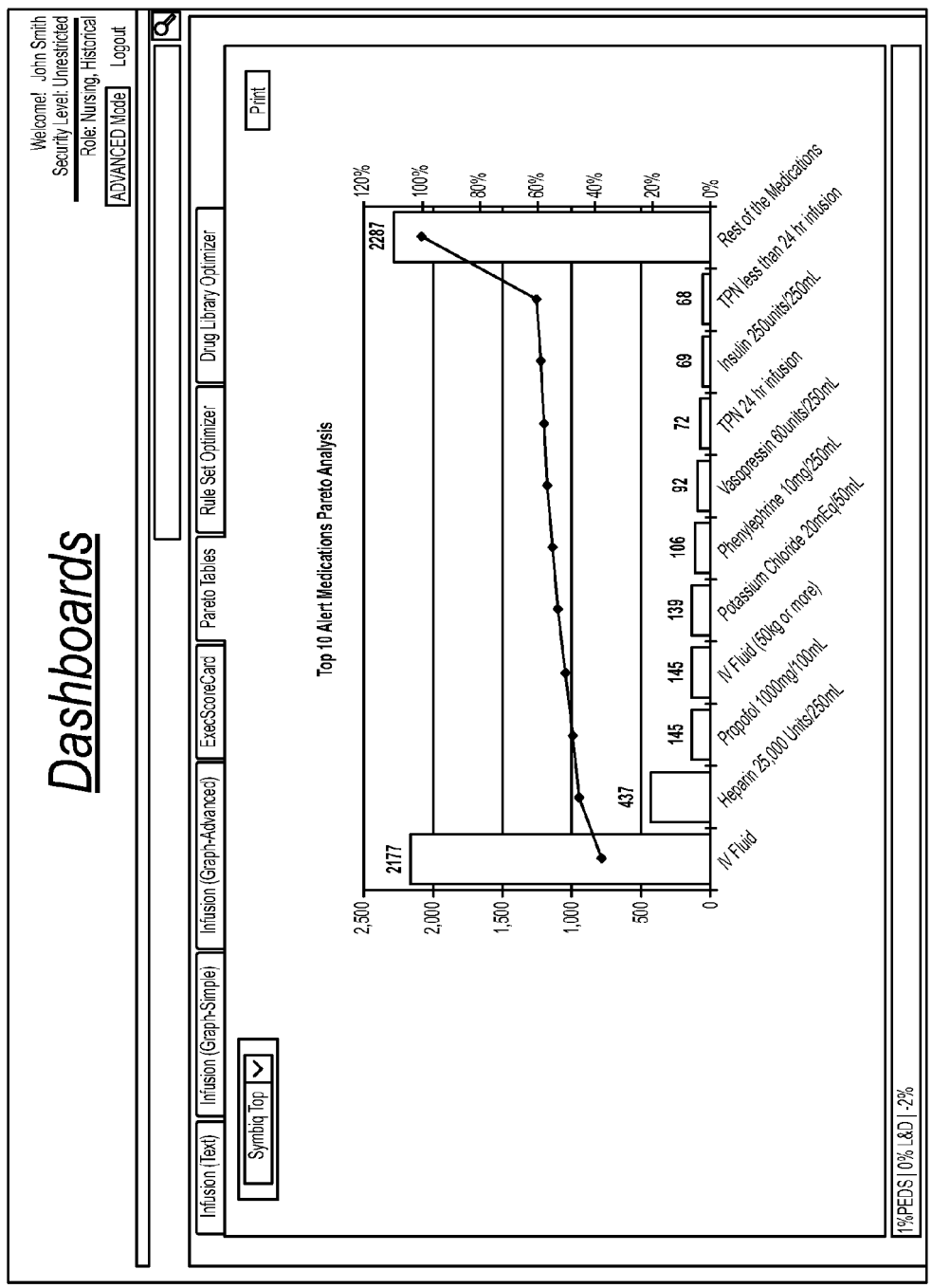
FIG. 12 illustrates an example screen shot of the data seen in FIG. 9 in a graphical format as a Pareto analysis chart or table.

An example screen shot of the Pareto analysis chart is shown in FIG. 12. The Pareto chart is the graphical display of the numeric data presented in the executive scorecard, showing individual values compared to a cumulative total. Any filter that has been applied in the generation of the executive scorecard will apply to or update the Pareto table. Furthermore, where the "ALL" filter has been used to generate the executive scorecard, additional filtering can be used or enabled for the Pareto chart. For example, if the ALL CCA/ ALL Infuser executive scorecard from FIG. 11 is used as the starting point, the Pareto chart in FIG. 12 can be prepared for a filtered set of "ALL CCA" data in which a SYMBIQ infusion system is the selected infuser type. The purpose of the Pareto chart is to highlight the most important among a (typically large) set of factors. The Pareto principle (also known as the 80-20 rule) states that, for many events, roughly 80% of the effects come from 20% of the causes. Applied to the hospital environment and specifically medication administration—roughly 20% of the Medications in the Drug Library will cause 80% of the alerts. Review of the Pareto chart will allow the user to save time by focusing on just a few medications when investigating deviations from established best practices. At the same time this investigation will be significant and efficient in that it will address a large number of alerts and potential medication administration issues An example screen shot of the rule set optimizer tab is shown in FIGS. 13A-B. The rule set optimizer filters and displays medication-related rule set entries from the drug library of one or more selected infusers and CCAs so that a clinician can review them. A hospital/doctor can enter limits of an amount of a drug that can be administered to provide clinicians a tool to help improve their own environment. Rules may be provided per drug, dose, department of hospital, etc., and may be upper/lower limits on drugs. The rule set optimizer interface may highlight potential sources that may cause unintended edits/overrides. The user is encouraged to review each entry carefully and make any changes as needed using a drug library editing tool such as HOSPIRA MED-NET™ software. Such a tool can be launched from or included with the dashboard. Rules may be provided per drug, dose, department of hospital, etc., and may be upper/lower limits on drugs. The rule set optimizer interface may highlight potential sources that may cause too frequent or unintended edits/overrides. Potential areas for further analysis and improvement include: limits are inconsistent/illogical/overlap, absence of hard limits or alerts, new drug concentration changes, overrides accepted out of habit, instances where nursing staff are pushing drugs more moderately than recommended, etc.

Figure 14:
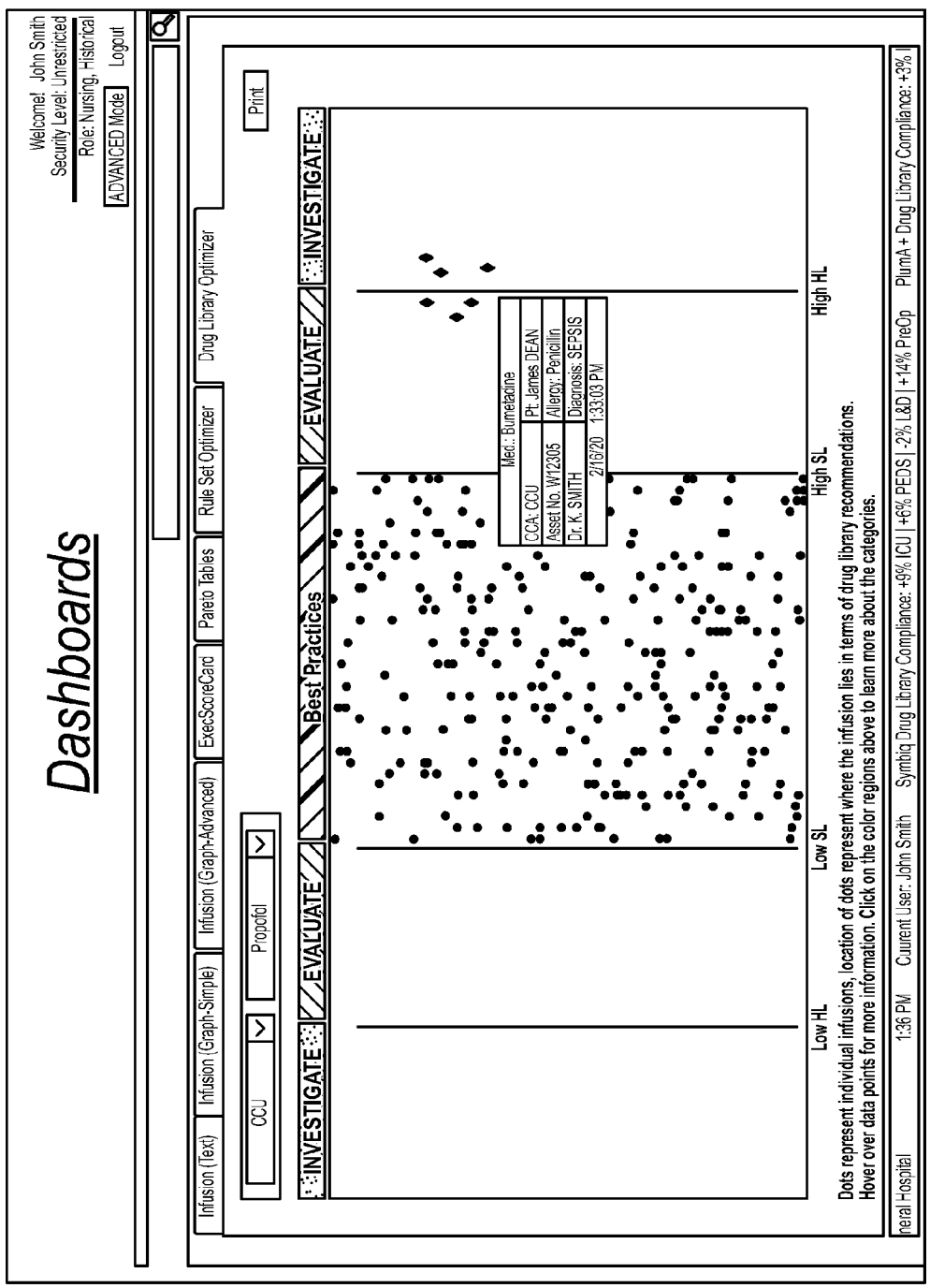

An example screen shot of the drug library optimizer tab is shown in FIG. 14. The drug library optimizer interface displays a histogram of all infusion events, each dot representing an infusion. The clinician is able to see quickly and easily which infusions fall into the hospitals established "best practice" or "green" limits and identify outliers. The outliers are further rated, plotted or spatially arranged by severity into "evaluate-yellow" and "investigate-red" categories. A user may mouse over the dots to see event details (e.g., including a type of medication infused, a clinical care area, an infuser asset number, a clinician and/or physician name, a date and time when event occurred/started, a patient name, allergy information regarding the patient or the medication, and diagnosis).

Events shown within the "best practice" range typically indicate the clinician did not encounter an alert when programming the infusion device. The yellow "evaluate" category would signify soft limit alerts and the red "investigate" category signifies hard limit alerts. Filters (such as CCA and medication) can be applied.

Users with permission access rights may enter alphanumeric type search criteria in the search field located in the upper right portion of the interface, e.g., as shown in the illustration in FIG. 14. For example, an asset number may be entered (i.e., W12305) for an infusion pump, and the dashboard system may search through a database and locate the pump and data pertaining to that pump. Once the dashboard locates the infusion pump, the dashboard may provide the simple graphical tab view, as shown for example in FIG. 15, and may indicate the infusion pump location via a flashing arrow—pointing to the located/identified infusion pump. The user now can hover over, or click-down to drill-down to receive desired information (e.g., alerts, location, asset number, serial number, etc.).

Figure 15:
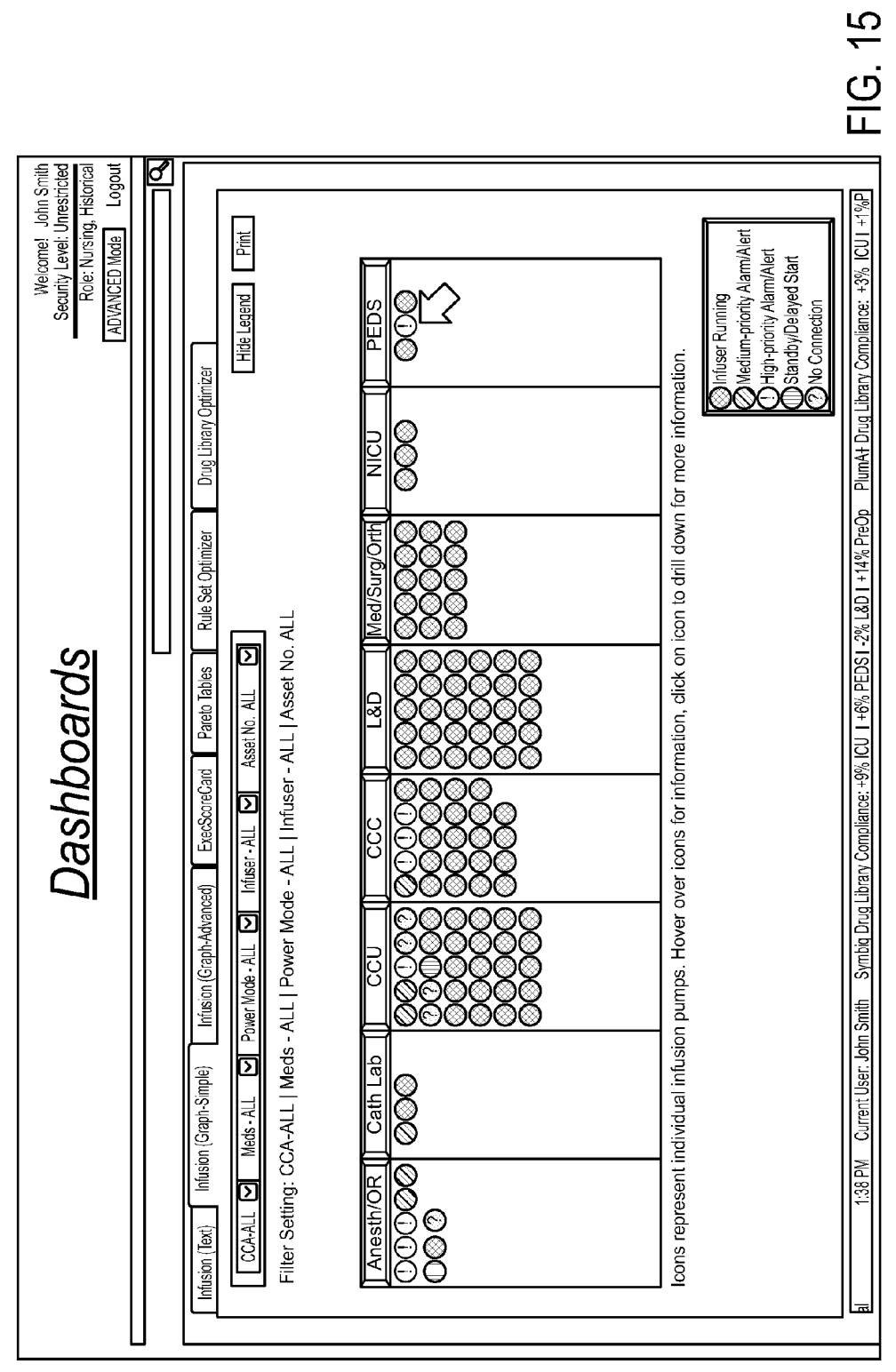

The example interfaces shown in FIGS. 14-15 enable a visual representation of medical devices operating conditions (e.g., operating within or outside of predetermined/preset limits). The interface may be configured to provide an alert indicating which medical devices are operating outside optimal conditions. The visual representations further illustrate icons/graphics in a meaningful manner, and the icons/graphics and interface provide functionality as well. For example, a graphical representation of icons of infusion pumps can be organized based on color and location within the interface to provide information to a user (e.g., dots represent infusion pumps/color indicates status, graphically show number of bags of pumps/color indicates channel of pump, dots represent an infusion event (drug library optimizer) to illustrate pumps within range of best practice). Positioning of icons in the graphical representations can provide information to a user and selection of items on or within the interface may provide additional information about the items, such as for example, selection of an icon associated with a medical device may return a map showing the location of the medical device and additional associated information.

In some examples, as shown within any of FIGS. 3-15, the graphical interface representation may include a data scroll at the bottom of the interface to provide various types of information about the hospital, user, time and date, operation of medical devices, such as trends in Drug Library compliance, etc.

Within examples described herein, a graphical interface platform is provided that receives data and provides reports in real-time and on a historical or trended basis to users. The graphical interface may be configured to determine medical devices operating outside of protocol, and may be configured according to filter parameters. For example, ad-hoc research may be performed by configuring filters of the graphical interface to determine operation of devices, administration of medications, etc. As a specific example, a user may research for trending in the past twenty-four hour period for usage of the drug heparin within a certain unit of a hospital. With regard to operating outside of protocol, a user can determine top ten errors or adverse events within a hospital.

The graphical interface may be configured to process received data to provide trending in real-time, such as nursing function oversight or why a dose of medication was prescribed when outside certain protocols. In examples, the interface may enable hospital personnel to readily identify infusion pumps that are operating outside of protocol or to identify practice trends regarding the use of pumps.

The graphical interface further enables CQI (continuous quality improvement) reporting, providing actionable data to support the caregiver at the bedside, improve medication administration safety and to avoid ADE's (adverse drug events) and potential patient harm. The graphical interface supports the user in identifying opportunity for drug library optimization.

The graphical interface may be further configured to provide notifications for any number of indicators, alerts, and alarms. The notifications can be provided in an escalated manner, such as to initially provide the notification to the bedside nurse, then to the charge nurse, then to the house or facility supervisor, etc.

The graphical interface may be further configured to enable searching for data, such as to search for a specific medical device and return a location of the device, information associated with use of the device, etc. The graphical interface may receive data from a number of systems in a hospital, and provide information related to census and patient acuity, ensuring the correct distribution and availability of infusion devices, etc. Further, the graphical interface may be configured to provide a two-dimensional or three-dimensional map of where a medical device is located. The map can include graphical representations of the medical devices in a particular area or volume of space. The graphical representations can be relatively simple geometric shapes such as dots, triangles or rectangles representing different medical devices or they may be digital or holographic images of the medical devices. As described herein the graphical representations of the medical devices on the map can be equipped with colors, text, symbols or other display characteristics that provide additional information, including but not limited to battery/AC status, alert/alarm status, no connection status, etc.

The graphical interface may be accessible via the Internet, an intranet or other web-based application. The graphical interface may be configured as shown in any of the examples described herein to provide a graphical representation of medical devices in which the graphical representation indicates information about the medical devices using color, icons, location of graphics, etc.

Within examples described herein, a graphical interface platform is provided that illustrates a number of types of information. Components of the graphical interface platform may be customizable in a drag/drop manner, such that components of the graphical interface platform include modules for display. For example, drag-and-drop includes action of (or support for the action of) selecting an object and dragging the object to a location in the interface or onto another object. Objects to be selected may include components of the graphical interface platform. The components of the graphical interface platform include any of the illustrations within FIGS. 3-15. For example, components may include the high-level infuser information shown in the table in FIG. 3, the columns of graphical illustrations shown in FIGS. 4-8 and FIG. 15, the executive scorecard tables shown in FIGS. 9-11, the Pareto table or chart shown in FIG. 12, the rule-set optimizer information tables shown in FIGS. 13A-B, or the columns of data as illustrated in FIG. 14. Thus, the graphical interface platform may be customizable to illustrate any number or combination of data as shown in any of FIGS. 3-15, for example.

It is further contemplated that the dashboard or graphical interface platform can be arranged to be customizable or configurable by the user to define the screens and screen content they find most relevant or helpful in their role. It should also be understood that while a "Top 10" approach has been taken on some screens, one or more approaches selected from a top 3, 5, 15, 20, 25, 50 or 100 approach could be implemented instead or as well.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Furthermore, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

What is claimed is:

1. A method comprising:
   receiving real-time data associated with operation of medical devices and location of the medical devices within an environment, wherein the location of the medical devices corresponds to a physical clinical care area in the environment;
   processing the data to determine medical devices operating within and outside of predetermined operating conditions of the medical devices;
   providing, by a computing device, on a display a graphical representation including multiple tabs and each tab selectable to provide operations of the medical devices organized based on the location of the medical devices within the environment, wherein a first tab provides a simple graphical representation of operations of the medical devices including an indication of one of medical devices operating within the predetermined conditions, medical devices operating outside of the predetermined conditions, and medical devices operating in a manner which indicates a potentially harmful physiological condition of a patient associated with the medical devices and organized based on the location of the medical devices within the environment, and a second tab provides an advanced graphical representation of operations of the medical devices including information related to operations of the medical devices and an indication of a number and a status of IV bags associated with respective medical devices;
   processing the data to determine trending of the operation of the medical devices over time based on control limits;
   providing, by the computing device, a third tab including a histogram of operations of the medical devices illustrating an amount of medical devices along a spectrum of operating within and outside of the predetermined operating conditions of the medical devices based on the control limits; and
   determining, from the histogram, a number of overrides of the control limits.

2. The method of claim 1, wherein the indication of a given medical device includes a least one icon.

3. A non-transitory computer-readable medium having stored thereon instructions executable by a computing device to cause the computing device to perform functions comprising:
   receiving real-time data associated with operation of medical devices and location of the medical devices within an environment, wherein the location of the medical devices corresponds to a physical clinical care area in the environment;
   processing the data to determine medical devices operating within and outside of predetermined operating conditions of the medical devices;

providing a graphical representation including multiple tabs and each tab selectable to provide operations of the medical devices organized based on the location of the medical devices within the environment, wherein a first tab provides a simple graphical representation of operations of the medical devices including one of an indication of medical devices operating within the predetermined conditions, medical devices operating outside of the predetermined conditions, and medical devices operating in a manner which indicates a potentially harmful physiological condition of a patient associated with the medical devices and organized based on the location of the medical devices within the environment, and a second tab provides an advanced graphical representation of operations of the medical devices including information related to operations of the medical devices and an indication of a number and a status of IV bags associated with respective medical devices;

processing the data to determine trending of the operation of the medical devices over time based on control limits;

providing a third tab including a histogram of operations of the medical devices illustrating an amount of medical devices along a spectrum of operating within and outside of the predetermined operating conditions of the medical devices based on the control limits; and determining, from the histogram, a number of overrides of the control limits.

4. A method comprising:

receiving real-time data associated with operation of medical devices;

processing the data to determine medical devices operating within and outside of predetermined operating conditions of the medical devices;

providing a graphical representation including multiple tabs and each tab selectable to provide operations of the medical devices, wherein tabs of the graphical representation are configured to have rows and columns, wherein each column includes information related to a given clinical care area of an environment and each row of a given column includes information related to a given medical device located in the given clinical care area, wherein a first tab provides a simple graphical representation of operations of the medical devices and a second tab provides an advanced graphical representation of operations of the medical devices including an indication of the operation of the medical device and an indication of a number and status of IV bags associated with the medical device;

communicating with the medical devices to determine the number and the status of the IV bags associated with the medical devices over time; and providing, as the indication of the operation of the medical device, an icon indicating one of in operation, infusion complete, and no connection, wherein the medical devices include infusion pumps and an indication of the number of IV bags associated with the medical device includes graphical icons, and wherein a color of the graphical icons indicates a channel of the infusion pump to which the IV bag is associated, and wherein the graphical icons representing the IV bags are colored so as to illustrate a current percentage filled condition of the IV bags.

5. The method of claim 4, wherein the information related to the given medical device includes graphical icons, and wherein a color of the graphical icons indicates a status of the medical device.

6. The method of claim 5, wherein the graphical icons are selectable to cause information retrieval functions to be performed and real-time data regarding the operation of the medical device associated with the selected graphical icon to be displayed.

7. A non-transitory computer-readable medium having stored thereon instructions executable by a computing device to cause the computing device to perform functions comprising:

receiving real-time data associated with operation of medical devices;

processing the data to determine medical devices operating within and outside of predetermined operating conditions of the medical devices;

providing a graphical representation including multiple tabs and each tab selectable to provide operations of the medical devices, wherein tabs of the graphical representation are configured to have rows and columns, wherein each column includes information related to a given clinical care area of an environment and each row of a given column includes information related to a given medical device located in the given clinical care area, wherein a first tab provides a simple graphical representation of operations of the medical devices and a second tab provides an advanced graphical representation of operations of the medical devices including an indication of the operation of the medical device and an indication of a number and status of IV bags associated with the medical device;

communicating with the medical devices to determine the number and the status of the IV bags associated with the medical devices over time; and providing, as the indication of the operation of the medical device, an icon indicating one of in operation, infusion complete, and no connection, wherein the medical devices include infusion pumps and an indication of the number of IV bags associated with the medical device includes graphical icons, and wherein a color of the graphical icons indicates a channel of the infusion pump to which the IV bag is associated, and wherein the graphical icons representing the IV bags are colored so as to illustrate a current percentage filled condition of the IV bags.

8. A method of monitoring and managing medical devices, the method comprising:

receiving real-time data associated with operation of medical devices and location of the medical devices within an environment, the data including at least one current condition associated with operation of the medical devices, wherein the location of the medical devices corresponds to a physical clinical care area of a plurality of physical clinical care areas in the environment;

processing the data to generate a display of the at least one current condition associated with operation of the medical devices;

providing on the display a graphical representation including multiple tabs and each tab selectable to provide specific operation information of at least some of the medical devices, wherein a first tab provides a simple graphical representation of operations of the medical devices including within and outside of predetermined operating conditions organized based on the location of the medical devices within the environment, and a second tab provides an advanced graphical representation of operations of the medical devices including information related to operations of the medical devices and an indication of a number and a status of IV bags associated with respective medical devices;

accumulating the real-time data received over time so as to form historical data;

processing the real-time data to determine trending of the operation of the medical devices over time based on control limits; and displaying a third selectable tab for generating historical reports, based on the historical data and the trending of the operation of the medical devices, accessible on the display that has a graphical visual representation of medications ranked by frequency of infusions of the medications by the medical devices, a number of alerts associated with said infusions, a percentage of alerts associated with said infusions, a number of overrides associated with said infusions, and a number of edits associated with said infusions for at least one physical clinical care area of the plurality of physical clinical care areas in the environment, wherein the graphical representation conveys summary information by including a visual indicator of the at least one current condition and is drill-down activatable for a given medical device such that when activated detailed information from the received real-time data is displayed for the given medical device, and based on selection of a given medication from the graphical visual representation of medications ranked by frequency of infusions, displaying an overlay window illustrating the infusions involving the given medication and a type of control limit violated causing the alert.

9. The method of claim 8, further comprising a step of displaying on the display at least one menu that allows a clinician/viewer to selectively filter the graphical representations to be displayed using a display filter selected from a group of display filters consisting of clinical care area, medication, medical device power mode, medical device and asset number.

10. The method of claim 9, wherein the display filter includes multiple display settings and includes a display setting that is all inclusive.

11. The method of claim 9, further comprising the steps of:
when the third selectable tab is activated by the clinician/viewer, providing on the display a time period selection menu for a clinician/viewer to use to define a time period of interest; and
generating on the display an ad hoc historical report relating to the operation of medical devices during the time period of interest based upon the historical data.

12. The method of claim 11, wherein the time period selection menu is provided as a drop-down menu that allows the clinician/viewer to selectively define the time period of interest as a time period selected from a group of time periods consisting of an hour, a series of consecutive hours, a portion of a predefined work shift, a predefined work shift, a day, a series of consecutive days, a week, a series of consecutive weeks, a month, a series of consecutive months, a quarter, a year, a series of consecutive years, and from a given beginning date to given ending date.

13. The method of claim 11, wherein the summary information, the detailed information and the third selectable tab for generating historical reports are all provided on a first screen of the display and are thereby initially accessible to the clinician/viewer without requiring navigation to a second screen.

14. The method of claim 8, further comprising a step of displaying on the display at least one menu that allows a clinician/viewer to selectively filter the graphical representations without first selecting a patient from the display.

15. The method of claim 8, wherein the activation of the graphical visual representation is accomplished by one of hovering a cursor over the graphical visual representation and clicking a cursor while the cursor is positioned on the graphical visual representation.

16. The method of claim 8, wherein the graphical representation of a given medical device includes a least one icon.

17. The method of claim 16, wherein the at least one icon is a circular dot.

18. The method of claim 8, wherein the at least one condition is one of medical devices operating within the predetermined conditions, medical devices operating outside of the predetermined conditions, and medical devices operating in a manner which indicates a physiological parameter of a patient deviating from a therapy goal.

* * * * *